United States Patent
Loype

(10) Patent No.: US 11,903,766 B2
(45) Date of Patent: Feb. 20, 2024

(54) SYSTEMS AND METHODS FOR A USER INTERFACE FOR A MEDICAL IMAGING SYSTEM

(71) Applicant: GE Precision Healthcare LLC, Milwaukee, WI (US)

(72) Inventor: Birger Loype, Horten (NO)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 67 days.

(21) Appl. No.: 17/210,294

(22) Filed: Mar. 23, 2021

(65) Prior Publication Data

US 2022/0304660 A1   Sep. 29, 2022

(51) Int. Cl.
*A61B 8/00*       (2006.01)
*A61B 8/12*       (2006.01)

(52) U.S. Cl.
CPC .............. *A61B 8/467* (2013.01); *A61B 8/12* (2013.01); *A61B 8/461* (2013.01); *A61B 8/54* (2013.01); *A61B 2560/0487* (2013.01)

(58) Field of Classification Search
CPC ........... A61B 8/467; A61B 8/12; A61B 8/461; A61B 8/54; A61B 2560/0487
See application file for complete search history.

(56) References Cited

U.S. PATENT DOCUMENTS

| | | | | |
|---|---|---|---|---|
| 5,402,793 A * | 4/1995 | Gruner | ................. | A61B 8/4461 600/463 |
| 5,774,187 A * | 6/1998 | Tsunoda | ................. | H04N 21/47 348/E9.04 |
| 9,245,441 B1 * | 1/2016 | Poojary | ................. | G08C 23/04 |
| 2006/0058654 A1 * | 3/2006 | Di Marco | ............ | A61B 8/4477 600/437 |
| 2012/0065508 A1 * | 3/2012 | Gerard | ................. | A61B 8/461 600/443 |
| 2015/0000025 A1 * | 1/2015 | clements | ................. | G06F 3/041 4/443 |

(Continued)

OTHER PUBLICATIONS

Wang, S. et al., "Robotic Ultrasound: View Planning, Tracking, and Automatic Acquisition of Trans-esophageal Echocardiography," IEEE Robotics & Automation Magazine, vol. 23, No. 4, Nov. 7, 2016, 15 pages.

*Primary Examiner* — Keith M Raymond
*Assistant Examiner* — Sean A Frith
(74) *Attorney, Agent, or Firm* — McCoy Russell LLP

(57) ABSTRACT

The current disclosure provides methods and systems for navigating among display panels and graphical elements of a user interface of a medical imaging system via controls of a handheld imaging device. In one embodiment, the current disclosure provides for a method comprising, in response to an operator of the medical imaging system adjusting one or more controls arranged on a control handle of a handheld ultrasound device of the medical imaging system, adjusting a focus of a user interface (UI) of the medical imaging system among a plurality of graphical control elements displayed in the UI; and in response to the operator selecting a graphical control element of the plurality of graphical control elements at a location of the focus of the UI via the one or more controls, executing an action of the medical imaging system associated with the selected graphical control element.

20 Claims, 11 Drawing Sheets

(56) References Cited

U.S. PATENT DOCUMENTS

| | | | |
|---|---|---|---|
| 2015/0073340 A1* | 3/2015 | Pacheco | A61B 34/76 |
| | | | 604/95.01 |
| 2016/0338590 A1* | 11/2016 | Sagalovich | A61B 1/07 |
| 2016/0345936 A1* | 12/2016 | Cho | G01S 7/52084 |
| 2017/0102871 A1* | 4/2017 | Won | G06F 9/451 |
| 2018/0085090 A1 | 3/2018 | Park et al. | |
| 2018/0310920 A1* | 11/2018 | Specht | G09B 23/286 |
| 2018/0322628 A1* | 11/2018 | Schroecker | G06T 7/0012 |
| 2019/0094659 A1* | 3/2019 | Misawa | H04N 5/23245 |
| 2019/0125302 A1* | 5/2019 | Clark | A61B 8/4488 |
| 2021/0038321 A1* | 2/2021 | Toporek | G06V 10/764 |
| 2022/0218306 A1* | 7/2022 | Peszynski | A61B 8/4466 |

\* cited by examiner

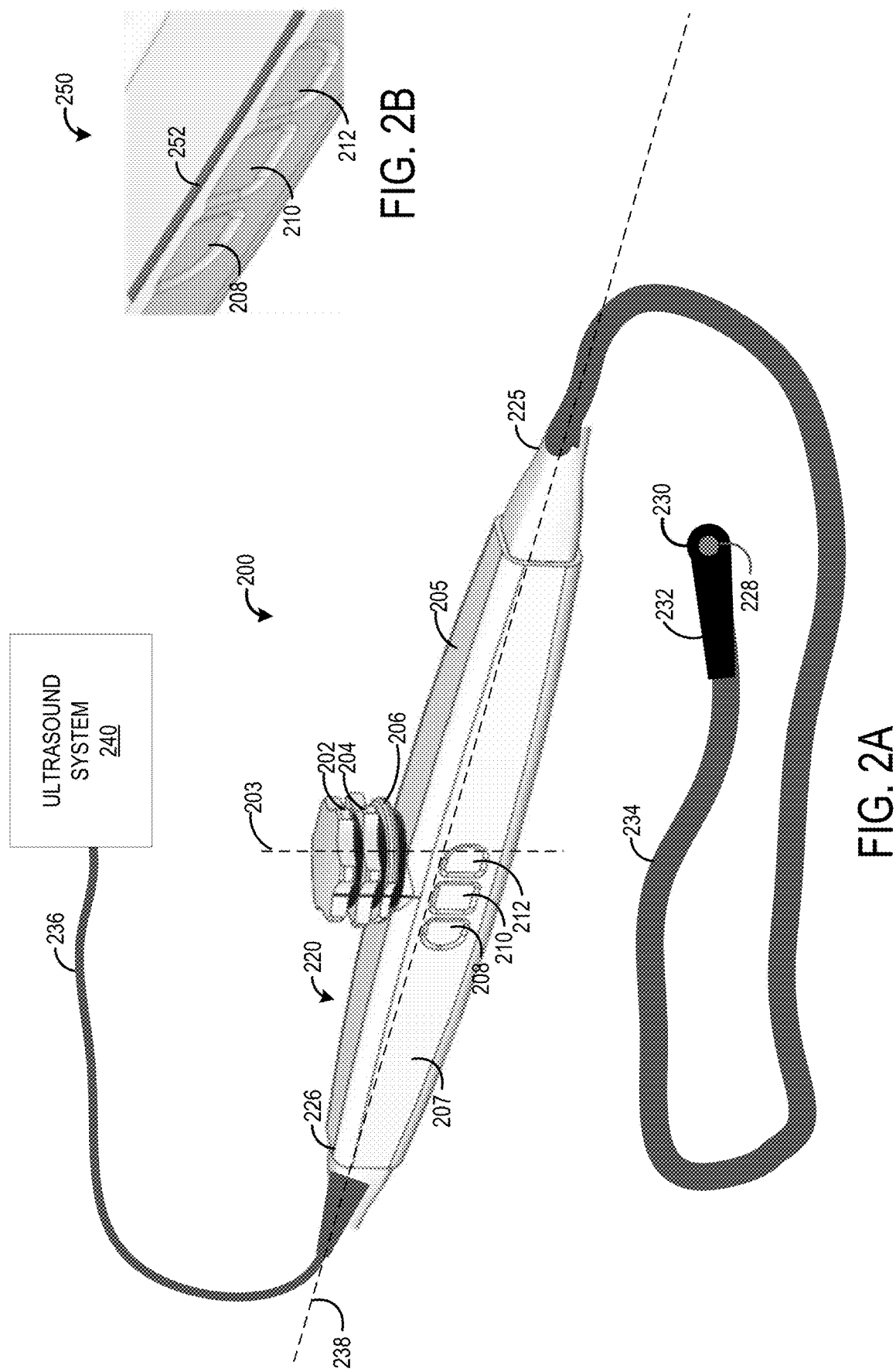

SYSTEMS AND METHODS FOR A USER INTERFACE FOR A MEDICAL IMAGING SYSTEM

TECHNICAL FIELD

Embodiments of the subject matter disclosed herein relate to medical imaging, and more particularly, to systems and methods for interacting with a user interface of a medical imaging system.

BACKGROUND

Medical imaging may be used to visualize an anatomical feature, such as soft tissue features or blood flow, inside a body of a patient during an examination. In some types of medical imaging, such as in endoscopic ultrasound imaging, an operator of a medical imaging system directs a probe coupled to a distal end of an insertion tube of a handheld ultrasound device into a cavity of the patient via a handle of the handheld ultrasound device. Signals generated by transducers of the probe are transmitted to the anatomical feature, and information about the anatomical feature is detected from signals reflected back from the anatomical feature, resulting in one or more images of the anatomical feature.

The insertion tube may be flexible enough to pass through the body cavity into a desired position, and the probe may be coupled to the insertion tube via a flexible neck assembly which may be flexed or bent to allow the probe to pass through curves in the body cavity. For example, in transesophageal echocardiography (TEE), the insertion tube follows curves of an esophagus of the patient to be placed at a suitable position for diagnosing diseases of the heart. To advance and manipulate the probe, the handheld ultrasound device may include one or more controls arranged on the handle. In one example, the controls include one or more control wheels, which may be rotated by the operator to flex or bend the flexible neck assembly in a left, right, posterior, or anterior direction. By advancing or withdrawing the probe via the handle, and adjusting the one or more control wheels, the transducers of the probe may be directed towards a region of interest (ROI) and tilted to optimize an acquisition of ultrasound images of the ROI, which may be displayed on a display device of the ultrasound system within a user interface (UI). Additionally, one or more buttons arranged on the handle of the handheld ultrasound device may allow the operator to interact with the UI. For example, the one or more buttons may permit the operator to capture and store a current image in an image store, or to switch between different displays of the UI, or to adjust one or more settings and/or parameters of the ultrasound system.

SUMMARY

In one embodiment, the current disclosure provides for a method comprising, in response to an operator of the medical imaging system adjusting one or more controls arranged on a control handle of a handheld ultrasound device of the medical imaging system, adjusting a focus of a user interface (UI) of the medical imaging system among a plurality of graphical control elements displayed in the UI; and in response to the operator selecting a graphical control element of the plurality of graphical control elements at a location of the focus of the UI via the one or more controls, executing an action of the medical imaging system associated with the selected graphical control element.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of this disclosure may be better understood upon reading the following detailed description and upon reference to the drawings in which:

FIG. 2A shows an example ultrasound probe.

FIG. 2B shows an exploded view of a portion of an ultrasound probe.

DETAILED DESCRIPTION

Figure 1:
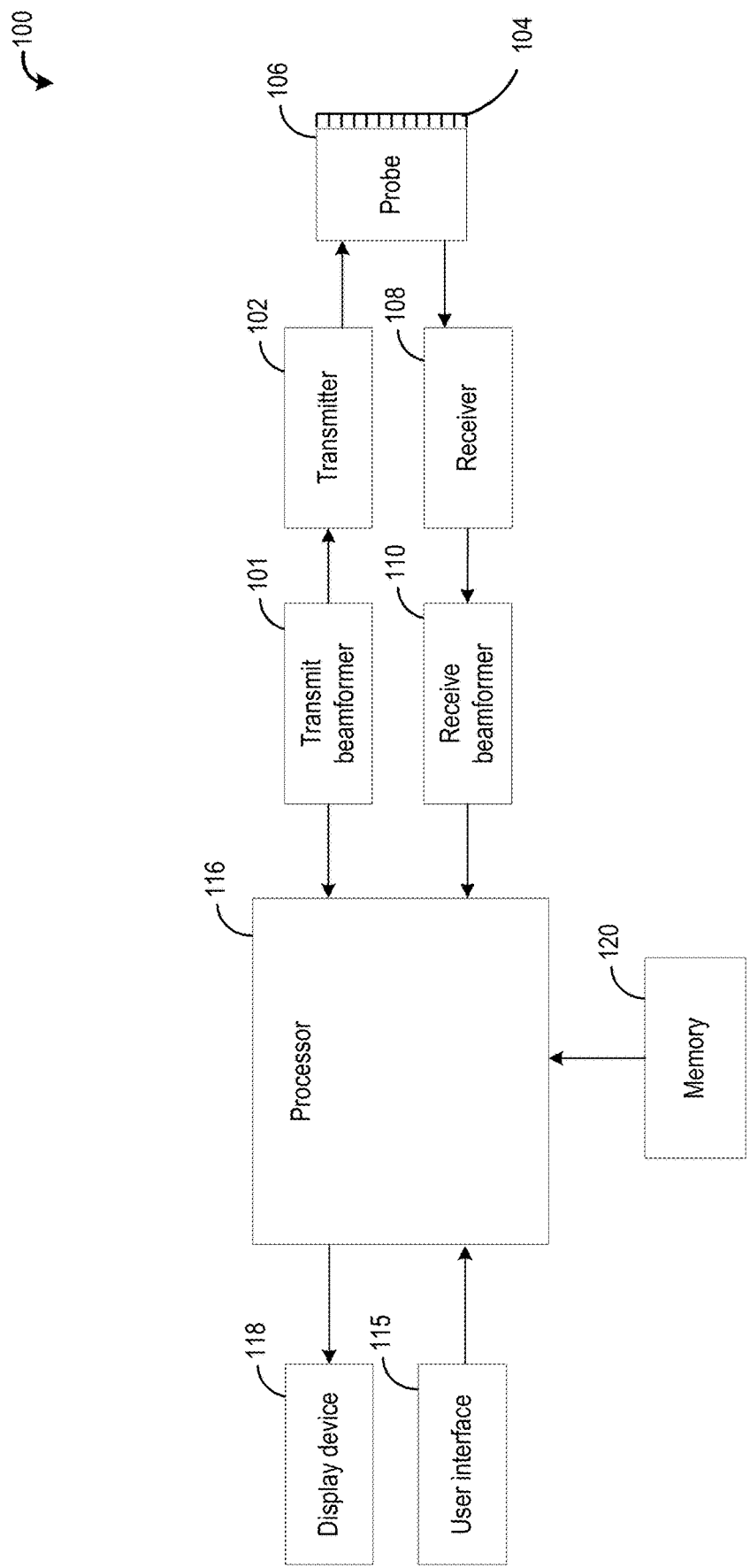
FIG. 1 shows a first block diagram of an exemplary embodiment of an ultrasound system.

The following description relates to methods and systems for interacting with a medical imaging system, such as an ultrasound imaging system, via one or more operator controls. The description herein is provided with respect to an ultrasound imaging system, although it should be appreciated the methods and systems may be adapted to any handheld imaging modality, such as optoacoustic/photoacoustic imaging, visible-light imaging, optical coherence tomography, etc., without departing from the scope of the disclosure.

Medical ultrasound imaging typically includes the placement of an ultrasound probe of an ultrasound imaging system, including one or more transducer elements onto or into an imaging subject, such as a patient, at a location of a target anatomical feature (e.g., heart, lung, etc.). Images are acquired by the ultrasound probe and are displayed on a display device in real time or near real time (e.g., the images are displayed once the images are generated and without intentional delay). The operator of the ultrasound probe may view the images and adjust a position of the ultrasound probe and/or various acquisition parameters (e.g., transmit frequency, transmit depth, time gain compensation, beam steering angle, beamforming strategy, etc.) in order to obtain high-quality images of the target anatomical feature. However, acquiring an optimal image (e.g., of desired quality) can be challenging, whereby manipulating the probe may entail paying careful attention to the images on the display device.

In some types of ultrasound imaging the probe is inserted into a body cavity of the patient, such as in trans-esophageal echocardiography (TEE), where a heart of the patient is imaged via a probe placed in an esophagus of the patient. In TEE ultrasound examinations, a handheld ultrasound device is used comprising a probe coupled to a TEE control handle via a rigid, flexible insertion tube, where the insertion tube is inserted into the esophagus using the TEE control handle. One or more controls may be arranged on the TEE control handle, where by manipulating the one or more controls, the operator may adjust an orientation and/or position of the probe in relation to the insertion tube. In one example, the operator adjusts a rotation of a control wheel to flex or bend an articulated neck assembly that couples the probe to the insertion tube to maneuver the probe in a direction (e.g., left or right, anterior or posterior). For example, to advance the probe along a downward and leftward curve of the esophagus, prior to advancing the probe, the operator may rotate a first control wheel in a first direction to flex the probe in a left direction (e.g., the patient's left), and the operator may rotate a second control wheel in a second direction to flex the probe in a posterior direction (e.g., towards the patient's back). By adjusting the position and/or orientation of the probe relative to the insertion tube prior to advancing the probe into the esophagus, an amount of friction between the probe and soft tissues of the esophagus may be reduced, thereby reducing any damage to the soft tissues and facilitating a placement of the probe. Further, a tilting of a lens of the probe may be adjusted to facilitate an acquisition of ultrasound images, for example, to ensure that an ultrasound beam of the ultrasound imaging system is perpendicular to a surface of a target object. Additionally, one or more buttons may be arranged on the probe handle that allow the operator to select one or more functionalities of the ultrasound imaging system (e.g., as shortcut buttons that are mapped to one or more functionalities available via a menu of the ultrasound imaging system.

However, one problem with the controls on the probe handle is that a mapping of the one or more buttons of the probe handle to one or more functionalities of the medical imaging system may not be indicated in the UI, whereby the operator may have to remember or memorize the mapping of the one or more buttons to the one or more functionalities. If the operator forgets which button has been selected, an attention of the operator may be directed away from the UI and towards the buttons to confirm a selected button, which may distract the operator from a task being performed during the examination, thereby reducing operator efficiency. Further, in some examples, the mapping of the one or more buttons on the probe handle to the one or more functionalities of the medical imaging system may be customizable between operators and imaging systems, which may make remembering the mapping more difficult. Further still, the buttons may be arranged on a side of the handle that is difficult to view while performing the ultrasound examination, whereby viewing the buttons may entail rotating or moving the handle, resulting in an undesired change of transducer/probe position. Yet a further issue is that while a cost and wall thickness of the probe handle may be reduced by replacing mechanical buttons on the handheld ultrasound device with capacitive sensor buttons, or resistive touch or force-sensing resistor buttons, or shorting pad buttons, operators may resist a transition to capacitive sensor buttons due to a loss of haptic feedback when a mechanical button or a spring dome that provides haptic feedback combined with the button technologies listed above is selected, which may aid the operators in determining when a button has been selected in a situation where no visual feedback is provided in the UI.

Additionally, when the operator rotates the control wheels to adjust a position of the probe by bending or tilting the flexible neck assembly, no indication of a degree to which the flexible neck assembly of the probe is bent or tilted may be displayed in the UI. To determine the degree to which the flexible neck assembly is bent, the operator relies on sensing a configuration of the wheels with a finger and/or thumb of the operator, which may result in confusion. A partial solution to this problem is proposed by Park et al in U.S. Pat. No. 20180085090, where a degree of tilt of the probe is displayed textually on a display device of the ultrasound system proximate the ultrasound images, or via an audio indication. However, reading the textual indication may entail a conscious attention of the operator, which may reduce an efficiency of the operator at manipulating the probe and/or increase an amount of time taken to perform the examination, while the audio indication may involve a conscious interaction with the user interface or may not be provided at a desired time, thereby reducing the efficiency of the operator.

In one embodiment, the current disclosure at least partially addresses the issues mentioned above via a method comprising, in response to an operator of the ultrasound imaging system adjusting one or more controls arranged on the probe handle, adjusting a focus of the UI of the ultrasound imaging system among a plurality of graphical control elements displayed in the UI. For the purposes of this disclosure, the focus is a pre-defined bounded area within the UI (e.g., a button, or a graphical component of the UI) that may receive input from the operator (e.g., via a mouse click, or via the one or more controls of the probe handle). The focus may be moved between or among a plurality of graphical components by the operator (e.g., via the one or more controls). For example, if the UI includes a horizontal row of five buttons, the operator may shift the focus from a first button to a second button positioned to the right of the first button by selecting a horizontal arrow key of a keyboard, or shift the focus from the second button to a third button positioned to the right of the second button by selecting the horizontal arrow key, and so on. When the focus is on a button of the horizontal row of five buttons, the operator may select the button on which the focus is set by selecting a different control.

Thus, in response to the operator selecting a graphical control element of the plurality of graphical control elements at a location of the focus of the UI via the one or more controls, an action of the ultrasound imaging system associated with the selected graphical control element is executed. In this way, by allowing the operator to navigate the plurality of shortcut control elements via the one or more controls and select a shortcut control element associated with a desired functionality, rather than mapping one or more buttons of the control handle to one or more functionalities, a number of shortcut control elements for quickly accessing functionalities of the medical imaging system may be increased and/or more easily customized, thereby increasing an efficiency of the operator in performing an ultrasound examination. Further, by highlighting the shortcut control element in focus, the operator may be provided with a visual cue to aid the operator in selecting the shortcut control element with the desired functionality and/or a visual indication of a current mode of operation of the medical imaging system. As a result of the visual cue and/or visual indication in the UI, a cognitive load of the operator during an examination (e.g., due to having to remember a functional mapping of the one or more buttons of the control handle to one or more functionalities) may be reduced, and a distraction of the operator due to having to examine the one or more controls of the control handle may be reduced, further increasing the efficiency of the operator. An additional advantage of the method is that by facilitating a more efficient interaction with the UI, mechanical buttons of the control handle may be replaced with capacitive sensor buttons, reducing a cost of the medical imaging system and/or ultrasound probe.

Additionally, as the operator adjusts a position and/or orientation of the probe during the examination, a display element of the UI may be adjusted to indicate the adjusted position and/or orientation of the ultrasound probe. For example, as the operator manipulates a first control wheel arranged on the handle to move the ultrasound probe in a first plane of freedom, and manipulates a second control wheel to move the ultrasound probe in a second plane of freedom, a visual indication of an angle of deflection of the ultrasound probe in the first plane of freedom and the second plane of freedom may be displayed on a graphical representation of the first control wheel in the UI and a graphical representation of the second control wheel in the UI, respectively. By providing the visual indication of the angle of deflection of the ultrasound probe in the first and second planes of freedom, rather than relying on the operator to sense a configuration of the first control wheel and the second control wheel with a thumb and finger of the operator, the cognitive load of the operator may be reduced and an efficiency of the operator may be increased.

As the operator manipulates the probe via the TEE control handle, ultrasound images acquired via a lens of the probe are displayed on a display device of the ultrasound imaging system. The images may be displayed within a user interface (UI) of the ultrasound imaging system, which may include additional display elements, such as an indication of a mode of the ultrasound system (e.g., B-mode, Doppler, etc.), a duration of the examination, and/or other parameters of the ultrasound imaging system such as transmit frequency, transmit depth, time gain compensation, beam steering angle, and so forth. In some examples, a textual description of the orientation and/or position of the probe in relation to the insertion tube may also be displayed in the UI. For example, an angle of tilt in one or more planes of freedom of the probe may be displayed in a panel of the UI, on a continuously updated basis, or in response to the angle of tilt exceeding one or more threshold angles. However, the textual description may be difficult to view while performing the examination, or may not be displayed at a time desired by the operator. If the textual description (or an audio indication) is not available to the operator in a desirable manner or at a desirable time, the operator may determine the orientation and/or position of the probe by sensing a rotational position of the first control wheel and the second control wheel with a finger and/or thumb of the operator, which may increase a cognitive load of the operator and reduce an efficiency of the operator at performing the examination.

The UI may also include an image store, wherein the operator may store one or more images (e.g., frames) selected during the examination. For example, the probe may be placed at a first location in the esophagus where a first desired image of the heart of the patient is acquired, and when the first desired image is acquired, the operator may select the first desired image and save it for later reference (e.g., for diagnosis, for showing the patient, for comparison purposes, etc.). When the operator saves the first desired image, the image may appear in the UI within the image store (e.g., a display element of the UI showing stored images). The probe may be subsequently placed at a second location in the esophagus where a second desired image of the heart of the patient is acquired, and when the second desired image is acquired, the operator may select the second desired image and save it for later reference. When the operator saves the second desired image, the image may appear in the UI within the image store (e.g., along with the first desired image). In this way, the operator may collect desired images while proceeding through the examination. If the operator wishes to view an image from the image store, the operator may select the image in the UI, whereby the selected image may be displayed in the UI.

In some examples, the additional display elements may be control elements, whereby the operator may interact with and/or change one or more settings of the ultrasound imaging system. The one or more settings may include display settings, such as whether to show or hide elements of a display on a screen the user interface. The one or more settings may include parameters of the ultrasound system, such as a type of ultrasound examination (e.g., B-mode, Doppler, etc.), or configuration parameters of a probe of the ultrasound imaging system. The operator may interact with, adjust, or select the control elements in the UI via a user input device, such as a mouse, touchpad, etc., or the operator may interact with the UI via a touchscreen, where the operator touches the display screen of the UI to interact with the UI. Further, in some examples, the TEE control handle may include one or more controls that allow the operator to interact with the UI. For example, the TEE control handle may include a touchpad and/or one or more buttons. By manipulating the touchpad and/or the one or more buttons, the operator may change a display of the UI, or a setting of the ultrasound imaging system. For example, the operator may select an image from the image store in the UI via a button on the TEE control handle. Examples of TEE handle controls are described in greater detail below in reference to FIGS. 2A and 2B, and FIGS. 3A-3D.

The one or more buttons may be mechanical buttons that have two states: a first, unselected state, where the mechanical button is not depressed, and a second, selected state, where the mechanical button is depressed. Thus, the operator may sense (e.g., with a finger or a thumb) when the mechanical button is selected or not based on a tactile feeling of the button. In another example, the buttons are mechanical buttons that do not have two states, where the operator may not sense (e.g., with a finger or a thumb) when the mechanical button is selected or not based on a tactile feeling of the button. However, in some examples, a visual indication may be provided that a mechanical button has been selected (e.g., the button or an outline of the button may be illuminated, etc.), whereby the operator may determine which of the one or more buttons has been selected. Additionally, when the operator selects a mechanical button, the operator may receive a haptic feedback that the mechanical button has been pressed, which may indicate to the operator that the mechanical button has been selected.

In yet another example, the one or more buttons are not mechanical buttons, but rather capacitive sensor buttons, where a pressing of the button is registered electronically by a sensor pad positioned under a surface of the button. For example, the button may have a surface made of plastic or similar material arranged over a sensor pad embedded in a softer material (e.g., foam, etc.). When the sensor pad is pressed, a conductive material is pressed against a printed circuit board (PCB) positioned under the sensor pad, thereby completing an electrical circuit that sends a signal (e.g., to the ultrasound system) that the button has been pressed. By using capacitive sensor buttons rather than mechanical buttons, fewer moveable parts may be used, reducing a cost of the ultrasound imaging system while increasing a reliability, cleanliness, and lifetime of the ultrasound imaging system. Additionally, capacitive sensor buttons offer increased flexibility in button shape and graphical representation.

However, one problem with using capacitive sensor buttons or similar technologies such as resistive touch, force-sensing resistor buttons, shorting pad buttons) is that confusion may be caused in an operator regarding a state of the buttons, since no haptic feedback is provided to indicate that a capacitive sensor button has been selected, and the operator may not be able to determine which of the one or more buttons has been selected via tactile sensing. Further, the operator may have to memorize a mapping of each button to a corresponding function in the ultrasound system.

As an example, the TEE control handle may have three buttons, corresponding to three different modes of operation, which may be pre-defined or configured by the user. For example, a first button may correspond to operation in a 2D mode, a second button may correspond to operation in a 4D mode, and a third button may correspond to operation in a Color mode. The operator may select the first button corresponding to operation in a 2D mode, and one or more elements of a display in the UI may update based on the selection. At a subsequent point in time, the operator may wish to switch to the 4D mode. However, the operator may forget whether the second button corresponds to the 4D mode or the third button corresponds to the 4D mode, or the operator may forget whether the current 2D mode was initiated by pressing the first button, the second button, or the third button. Because the capacitive sensor buttons provide no tactile indication of which button is selected, a tactile sensing of the buttons may not aid the operator in remembering which button to press. Additionally, the operator may not wish to rotate the TEE control handle to view the buttons to determine whether the first button, the second button, or the third button is illuminated, because rotating the TEE control handle may change a position of the probe (e.g., from a desired position to an undesired position). As a result of not remembering which button to select to switch to the 4D mode, the operator may be distracted from the examination, and/or may have to determine which button corresponds to the 4D mode by trial and error, distracting the operator from the examination, wasting time, and increasing a wear on the buttons.

In one example, the issues of not being able to easily and quickly view a mode of operation of the ultrasound imaging system, a rotational position of the first and/or second control wheels, and/or one or more shortcut options for accessing one or more functionalities of the ultrasound imaging system may be addressed by a medical imaging system comprising an ultrasound probe coupled to a TEE control handle via an insertion tube with an articulated neck mechanism, a display device, and a processor communicably coupled to the TEE control handle and the display device, and including instructions stored in a non-transitory memory that when executed cause the processor to, in response to an operator of the medical imaging system adjusting a first set of controls arranged on the TEE control handle, flex the articulated neck mechanism to adjust a position and/or orientation of the ultrasound probe; adjust a graphical display element of a user interface (UI) of the medical imaging system to indicate the adjusted position and/or orientation of the ultrasound probe; in response to the operator adjusting a second set of controls arranged on the TEE control handle in a first manner, adjust a focus of the UI between a plurality of display panels of the UI; in response to the operator adjusting the second set of controls in a second manner, adjust a focus of the UI between a plurality of control elements of the UI; indicate a location of the adjusted focus of the UI in the UI; and in response to the operator selecting a control element at the location of the adjusted focus via the second set of controls, execute a functionality of the medical imaging system associated with the control element. In this way, the operator may maintain attention on the ultrasound images and/or other elements of the UI while receiving visual feedback on a selection of a functionalities, parameters, settings, display options, etc. available to the operator.

Figure 3B:
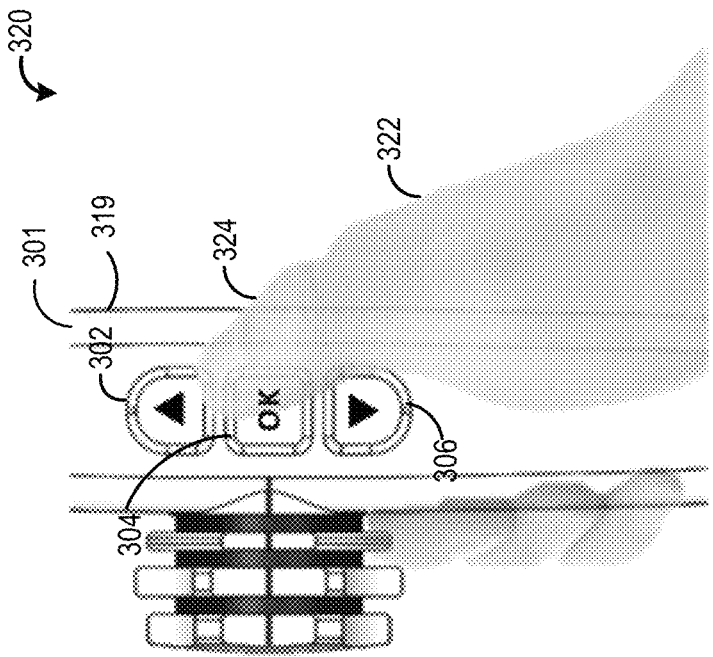
FIG. 3B shows an orientation of the first set of controls on a handle of an ultrasound probe when held by an operator of an ultrasound system.
Figure 3A:
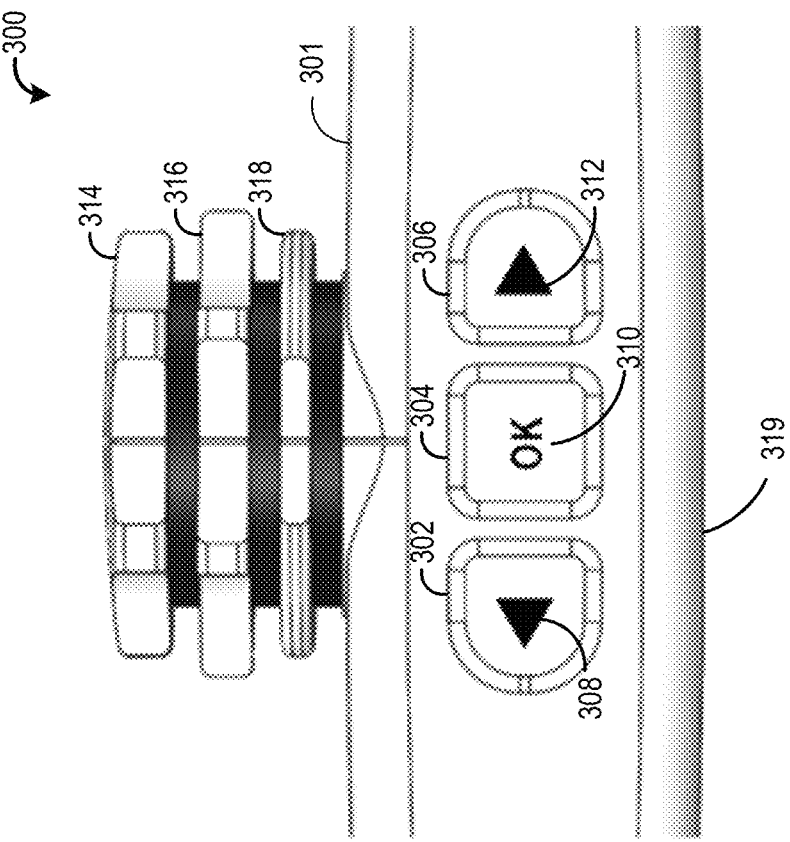
FIG. 3A shows a first example configuration of a set of controls on a handle of an ultrasound probe.
Figure 3D:
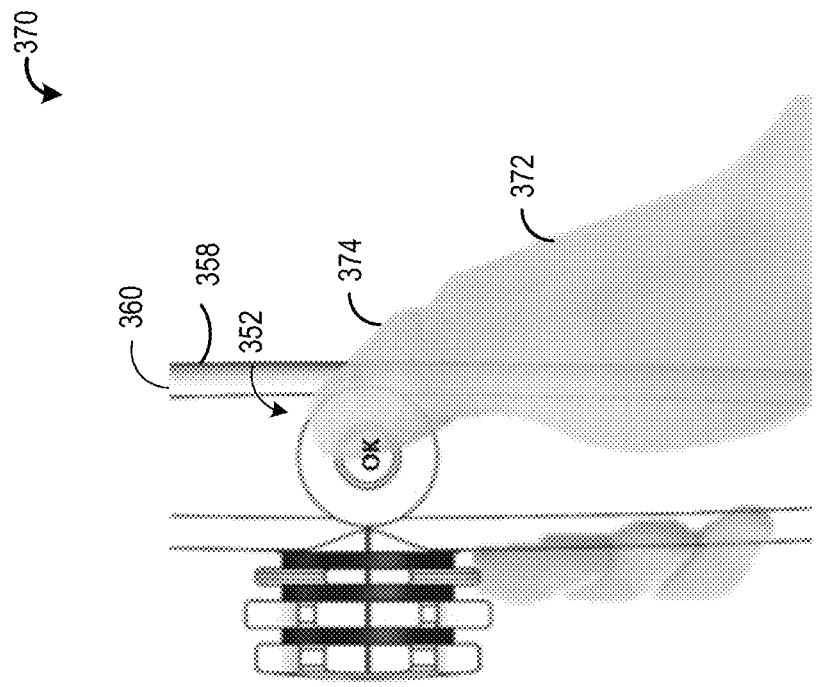
FIG. 3D shows an orientation of the second set of controls on a handle of an ultrasound probe when held by an operator of an ultrasound system.
Figure 3C:
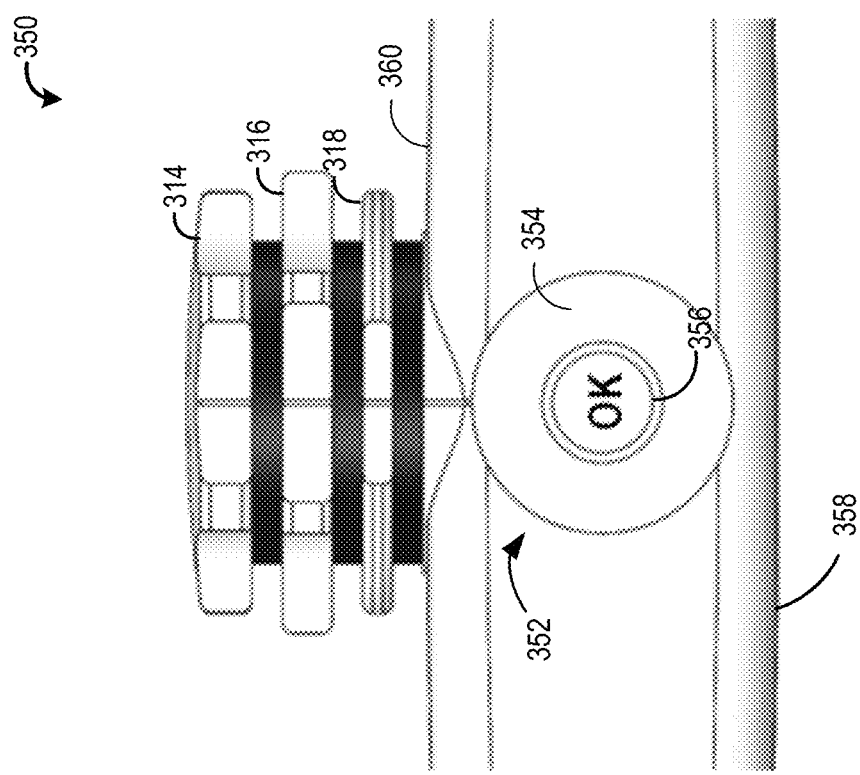
FIG. 3C shows a second example configuration of a set of controls on a handle of an ultrasound probe.

An example ultrasound imaging system is described below in reference to FIG. 1. The ultrasound imaging system may include a handheld ultrasound device, such as the handheld ultrasound device 200 of FIG. 2A. The handheld ultrasound device may include one or more controls on a handle of the handheld ultrasound device, including one or more capacitive sensor buttons, as shown by FIG. 2B. The one or more controls may be configured in a first example configuration, as shown in FIG. 3A, where the one or more controls may be manipulated by a hand of the operator as shown in FIG. 3B. A second example configuration of the one or more controls is shown in FIG. 3C, where the one or more controls may be manipulated by a hand of the operator as shown in FIG. 3D. The one or more controls may be used to select a mode of the ultrasound imaging system, where the mode options for selection and the selected mode may be displayed as shown in the example UI of FIG. 4A. The one or more controls may be used to save one or more images of the ultrasound images (e.g., for later reference), and to toggle between display elements of the UI, such as an image store, where images of the image store may be selected via the one or more controls, and a mode display, where one or more modes may be selected via the one or more controls, as shown in the example UI of FIG. 4B. The one or more controls may be used to toggle between each of the image store and the mode display and a third display element with selectable items, as shown by FIG. 4C. The UI may also include a graphical representation of a position of one or more control wheels of the handheld ultrasound device 200, as shown in FIG. 5A in relation to a configuration of the one or more controls indicated in FIG. 5B. The graphical representation of the position of the one or more control wheels may be configured as shown in the alternative configurations of FIG. 5C, and FIG. 5D. Modes of operation, parameters, and settings of the ultrasound imaging system may be adjusted via the first example configuration of the one or more controls of FIG. 3A in accordance with the procedure described by method 600 of FIG. 6. Modes of operation, parameters, and settings of the ultrasound imaging system may be adjusted via the second example configuration of the one or more controls of FIG. 3C in accordance with the procedure described by method 700 of FIG. 7. The graphical representation of the position of the one or more control wheels of the handheld ultrasound device 200 shown in FIG. 5A may be updated in accordance with the procedure described by method 800 of FIG. 8.

Referring now to FIG. 1, a schematic diagram is shown of an ultrasound imaging system 100 in accordance with an embodiment of the disclosure. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body of a patient (not shown). The probe 106 may be a one-dimensional transducer array probe with a one-dimensional (1D) transducer array structure, or may be a two-dimensional matrix transducer array probe with a two-dimensional (2D) transducer array structure. The transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams. In another example, the ultrasonic transducers are capacitive micro-machined ultrasonic transducers (CMUT). In some examples, the probe 106 is a portable handheld probe that may be manipulated by an operator on a surface (e.g., on a skin) of the patient. In other examples, the probe 106 is coupled to a distal end of a tube of a handheld ultrasound device, where the tube may be directed into a body cavity of the patient (e.g., during an endoscopic procedure) via a handle positioned at an opposite end of the tube from the probe 106, as described in greater detail below in reference to FIG. 2A.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry configured to perform all or part of the transmit beamforming and/or the receive beamforming. For example, all or part of the transmit beamformer 101, the transmitter 102, the receiver 108, and the receive beamformer 110 may be situated within the probe 106, or within another part of the handheld ultrasound device or the medical imaging system. The terms "scan" or "scanning" may also be used in this disclosure to refer to acquiring data through the process of transmitting and receiving ultrasonic signals.

A user interface 115 may be used to control operation of the ultrasound imaging system 100. The user interface 115 may include one or more of the following: a rotary element, a mouse, a keyboard, a trackball, a touchscreen, hard keys linked to specific actions, soft keys that may be configured to control different functions, and/or a graphical user interface displayed on a display device 118. The display device 118 may display a generated ultrasound image and various pieces of information processed by the ultrasound imaging system 100. In some examples, the user interface 115 may be integrated into the display device 118, for example, as a touch screen.

The ultrasound imaging system 100 includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the operations of the ultrasound imaging system 100 and flow of signals between the internal elements of the ultrasound imaging system 100. For example, the processor 116 may control the operation of the ultrasound imaging system 100 by receiving a control signal from the user input device 116.

The processor 116 may control the probe 106 to acquire data according to instructions stored on a memory 120. As discussed herein, memory includes any non-transient computer readable medium in which programming instructions are stored. For the purposes of this disclosure, the term tangible computer readable medium is expressly defined to include any type of computer readable storage. The example methods and systems may be implemented using coded instruction (e.g., computer readable instructions) stored on a non-transient computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include any other medium which can be used to store the desired electronic format of information and which can be accessed by the processor or processors or at least a portion of a computing device.

The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

In one example, the probe 106 includes a 2D transducer array, and the processor 116 calculates a time delay value for digital beamforming with respect to one or more sub-arrays included in the 2D transducer array. For example, the processor 116 may calculate a time delay value for analog beamforming for each of the transducers included in any one sub-array of the one or more sub-arrays. In one example, the transmitter 102 is an analog transmitter, the receiver is a digital receiver, and the processor 116 controls the analog transmitter 102 and the digital receiver 108 to form a transmission signal to be applied to each of the transducers, according to the time delay values for analog beamforming and digital beamforming. The processor 116 may control the analog transmitter 102 to add signals received from the transducers for each sub-array of the one or more sub-arrays, according to the time delay value for analog beamforming. Additionally, the processor 116 may perform analog to digital conversion of the signals added for each sub-array. The processor 116 may control the digital receiver 108 to generate ultrasound data by adding the digitized signals according to the time delay value for digital beamforming, and/or the processor 116 may control the analog transmitter 102 to classify the transducers to be included in the sub-arrays, apply the time delay value for performing analog beamforming, and add the signals for each of the sub-arrays. The processor 116 may control the analog transmitter 102 to add again synthesized signals generated by adding the signals for each sub-array by applying the time delay value for performing analog beamforming.

The processor 116 may be adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld and/or endoscopic probe in electronic communication with the handheld ultrasound imaging device, to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current medical imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

It should be understood that the ultrasound imaging system 100 shown in FIG. 1 is for illustration, not for limitation. Another ultrasound imaging system may include more, fewer, or different components.

Referring now to FIG. 2A, an example handheld ultrasound device 200 is shown, where the handheld ultrasound device 200 is electronically coupled to an ultrasound system 240 via a cable 236. In one example, the handheld ultrasound device 200 is a non-limiting example of the user interface 115 of the ultrasound system of FIG. 1. In the depicted example, the handheld ultrasound device 200 is a TEE ultrasound device comprising a control handle 220, which is flexibly coupled to a probe 230 via an insertion tube 234 on an opposite end of the control handle 220 as the cable 236. The probe 230 may be a non-limiting example of the probe 106 of FIG. 1. The cable 236 may be coupled to the control handle 220 via a strain relief 226, which may protect an electrical coupling of the cable 236 with the control handle 220 from a mechanical force applied to the insertion tube cable 236. The probe 230 may be configured to transmit ultrasound signals toward an object and receive ultrasound echo signals reflected from the object in order to obtain one or more images of an internal area of the object. The probe 230 may include one or more arrays of ultrasonic transducers (not shown in FIG. 2A).

The insertion tube 234 may be made of an elastic material with sufficient flexibility to follow a curved path through the esophagus, and sufficient rigidity to be advanced by an operator via the control handle 220. In one example, the insertion tube 234 has a length of 100-110 cm and a diameter of 10-20 mm. The insertion tube 234 may house cables for sending and receiving signals sent to the probe 230 from an ultrasound transceiver of the ultrasound system 240 and back to the ultrasound transceiver from the probe 230. The insertion tube 234 may be coupled to the control handle 220 via a strain relief 225, which may protect an electrical coupling of the cables with the control handle 220 from a mechanical force applied to the insertion tube 234.

The probe 230 may be coupled to the insertion tube 234 via a neck assembly 232, which may be a bendable, articulated mechanism arranged between the probe 230 and the insertion tube 234. The neck assembly 232 may be made of a metal, or another material with a similar thermal conductivity and specific strength, and may have an outer surface coated with an elastic material similar to that of the insertion tube 234. In one example, the bendable articulation mechanism is comprised of a plurality of hollow segments connected by one or more wires that lead to the control handle 220, such that the neck assembly 232 may be flexed in one or more directions by manipulating the one or more wires (e.g., via controls on the control handle 220). By flexing the neck assembly 232 in different configurations, the probe 230 may follow a curved passage through the esophagus for placement at a desired position. In other examples, wires may not be used, and the neck assembly 232 may be flexed in a different manner.

The flexing of the neck assembly 232 may be controlled by one or more controls arranged on the control handle 220, such as a first control wheel 202 and a second control wheel 204. In one example, the first control wheel 202 is positioned vertically on top of the second control wheel 204 on a top side 205 of the control handle 220, coaxially arranged along a vertical axis 203. The first control wheel 202 and the second control wheel 204 may be rotated by the operator via a finger and/or a thumb of the operator, where the first control wheel 202 controls a flexing or deflection of the neck assembly 232 in a first plane of freedom (e.g., a left direction or a right direction), and the second control wheel controls a flexing or deflection of the neck assembly 232 in a second plane of freedom (e.g., a posterior direction or an anterior direction). In one example, the neck assembly 232 may be bent at an angle of up to 180° in any of the left, right, posterior, and/or anterior directions (e.g., 360° of freedom in each plane of freedom).

For example, the operator may rotate the first control wheel 202 in a clockwise direction, thereby commanding a deflection of the neck assembly 232 towards a right side of a patient, or the operator may rotate the first control wheel 202 in a counter-clockwise direction, thereby commanding a deflection of the neck assembly 232 towards a left side of the patient (e.g., movement in the first plane of freedom). The operator may rotate the second control wheel 204 in a clockwise direction, thereby commanding a deflection of the distal end of the probe towards a front side of the patient, or the operator may rotate the second control wheel 204 in a counter-clockwise direction, thereby commanding a deflection of the neck assembly 232 towards a back side of the patient (e.g., movement in the second plane of freedom). Thus, by adjusting a rotational position of the first control wheel 202 and the second control wheel 204, and advancing or withdrawing the probe 230 via the control handle 220 (e.g., movement in a third plane of freedom), the operator may manipulate the probe 230 with three degrees of freedom (e.g., left-right, forward-backward, and up-down). Further, in some examples, by rotating the control handle 220 around a central axis 238, a lens 228 of the probe 230 may be rotated, allowing the operator to manipulate the probe 230 with six degrees of freedom (e.g., adding pitch, yaw, and roll).

The control handle 220 may also include a control wheel lock 206, which may lock a position of the first control wheel 202 and the second control wheel 204. For example, the control wheel lock 206 may be adjusted from a neutral position to a first position to lock the first control wheel 202 and the second control wheel 204, or the control wheel lock 206 may be adjusted from a neutral position to a first position to lock the first control wheel 202 and not the second control wheel 204, and may be adjusted to a second position to lock the second control wheel 204 and not the first control wheel 202, and may be adjusted to a third position to lock both the first control wheel 202 and the second control wheel 204. Both the first control wheel 202 and the second control wheel 204 may be unlocked by adjusting the control wheel lock 206 back to the neutral position.

The control handle 220 may include one or more control buttons, such as a first button 208, a second button 210, and a third button 212 of the control handle 220. In one example, the first button 208, the second button 210, and the third button 212 are arranged on a first side 207 of the control handle 220, where the first side 207 is easily accessed by a thumb of a right-handed operator while manipulating the probe 230 via the control handle 220. In another example, the first button 208, the second button 210, and the third button 212 may be arranged on a second side of the control handle 220, where the second side of the control handle 220 is opposite the first side of the control handle 220, and where the second side is easily accessed by a thumb of a left-handed operator while manipulating the probe 230 via the control handle 220. In still other examples, the first button 208, the second button 210, and the third button 212 may be arranged on a different side (e.g., not the first side or the second side) of the control handle 220.

In one example, the first button 208, the second button 210, and the third button 212 are arranged below and/or proximate the control wheel 202 and the control wheel 204, whereby a thumb of the operator may be easily moved between the control wheels 202 and 204 and the buttons. In other examples, the first button 208, the second button 210, and the third button 212 may not be arranged proximate the control wheel 202 and the control wheel 204, and/or may be arranged in a different position on a side of the control handle 202. For example, the first button 208, the second button 210, and the third button 212 may be arranged closer or farther to the insertion tube 234 than depicted in FIG. 2A, or higher or lower on the first side 207 than depicted in FIG. 2A. In some examples, the control wheels 202 and 204 may also be arranged closer or farther to the insertion tube 234 than depicted in FIG. 2A. Further, a spacing between the first button 208, the second button 210, and the third button 212 may be close together, as depicted in FIG. 2A (e.g. to allow for easy access by the thumb of the operator), or the spacing between the first button 208, the second button 210, and the third button 212 may be farther apart (e.g. to allow for easily discerning between different buttons).

FIG. 2B shows an exploded view of a portion of the control handle 220, in an example where the first button 208, the second button 210, and the third button 212 are capacitive sensor buttons. A capacitive-sensing board 252 is shown behind the first button 208, the second button 210, and the third button 212. As described above, when a capacitive sensor buttons is pressed, an electrical circuit of the capacitive-sensing board 252 is completed, which sends a signal to the ultrasound imaging system.

Turning now to FIG. 3A, a first example configuration of a set of controls 300 of a TEE control handle 301 of an ultrasound imaging system is shown, in accordance with an embodiment. The ultrasound imaging system may be a non-limiting example of the ultrasound imaging system 200 of FIG. 28, and the TEE control handle 301 may be a non-limiting example of the TEE control handle 220 of FIG. 2A. The first example configuration of the set of controls 300 includes a first button 302, a second button 304, and a third button 306, arranged on a side of the TEE control handle 301, below a first control wheel 314 (e.g., the first control wheel 202 of FIG. 2A), a second control wheel 316 (e.g., the second control wheel 204 of FIG. 2A), and a control wheel lock 318 (e.g., the control wheel lock 206 of FIG. 2A), where the first control wheel 314 and the second control wheel 316 are coaxially arranged on a top side of the TEE control handle 301. In the depicted example, the control wheel lock 318 is coaxially arranged with the first control wheel 314 and the second control wheel 316, although in other embodiments, the control wheel lock 318 may be arranged at a different location on the TEE control handle 301. For example, the control wheel lock 318 may be placed on a different side of the TEE control handle 301, or in a non-coaxial position with the first control wheel 314 and the second control wheel 316. In still other examples, the lock may be a button on a side of the TEE control handle 301.

In the first example configuration of the set of controls 300, the first button 302 is a back button, as indicated by a backward pointing arrow 308 on the first button 302. The second button 304 is a selection button, as indicated by the OK label 310. The third button 306 is a forward button, as indicated by a forward pointing arrow 312 on the third button 306. In one example, when the TEE control handle 301 is being used by an operator, the TEE control handle 301 is held by the operator with a bottom surface 319 of the TEE control handle 301 against a palm of the operator, such that the first button 302, second button 304, and third button 306 may be manipulated by a thumb of the operator.

Referring briefly to FIG. 3B, a view 320 of the first example configuration of a set of controls 300 shows an orientation of the first button 302, second button 304, and third button 306 when the TEE control handle 301 is being used by an operator, where a hand 322 of the operator 322 grips the TEE control handle 301 with the palm of the operator against the bottom surface 319 of the TEE control handle 301. When holding the TEE control handle as shown in the view 320, a thumb 324 of the operator may be positioned above the first button 302, second button 304, and third button 306, where the first button 302, second button 304, and third button 306 are within a comfortable range of the thumb 324.

The first button 302 (e.g., the back button), second button 304 (e.g., the selection button), and third button 306 (e.g., the forward button) may be functionally mapped to one or more actions in a user interface of the ultrasound imaging system, as described below in reference to FIG. 4A.

Figure 4A:
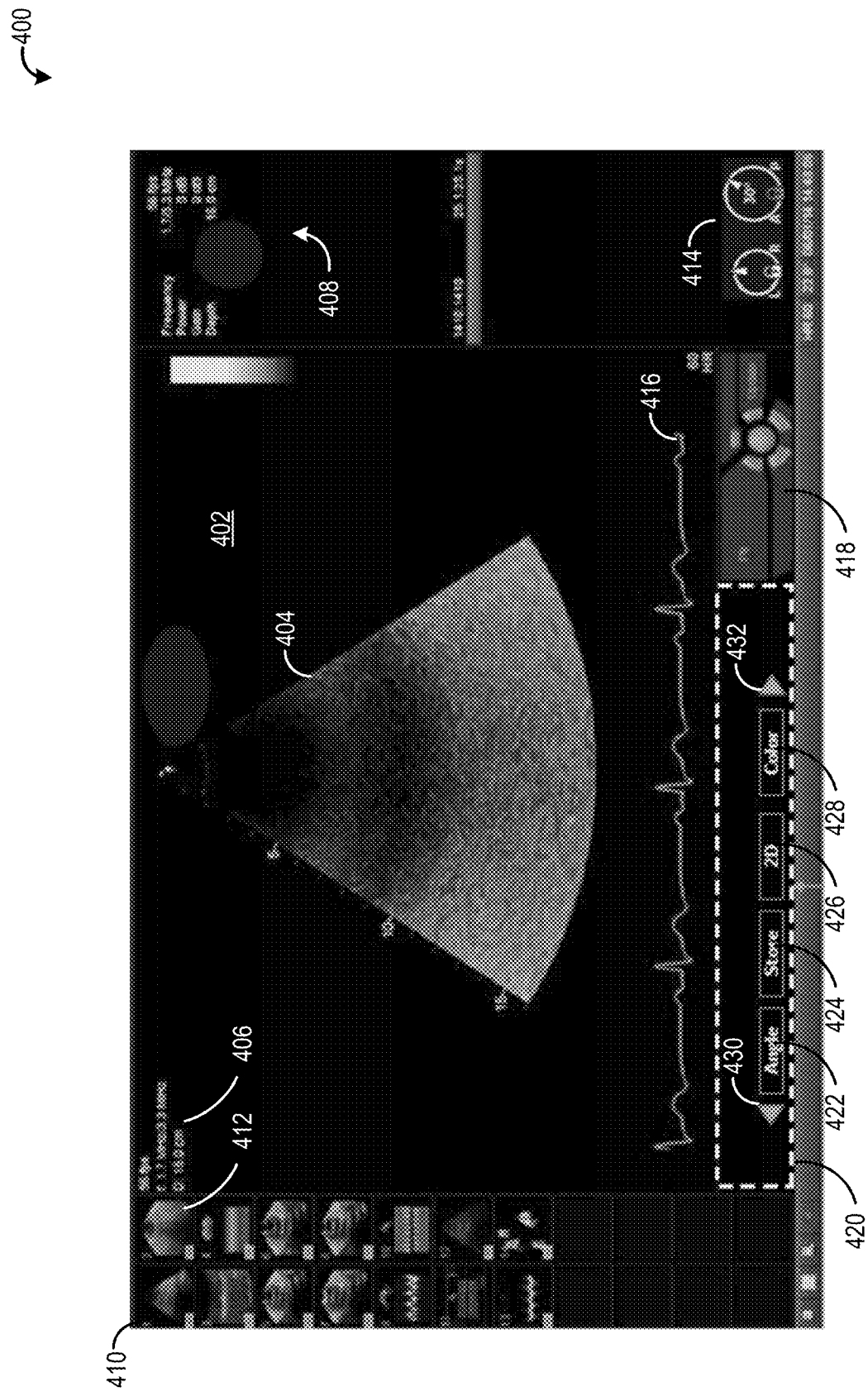
FIG. 4A shows an example user interface of an ultrasound system in a first configuration.
Figure 5A:
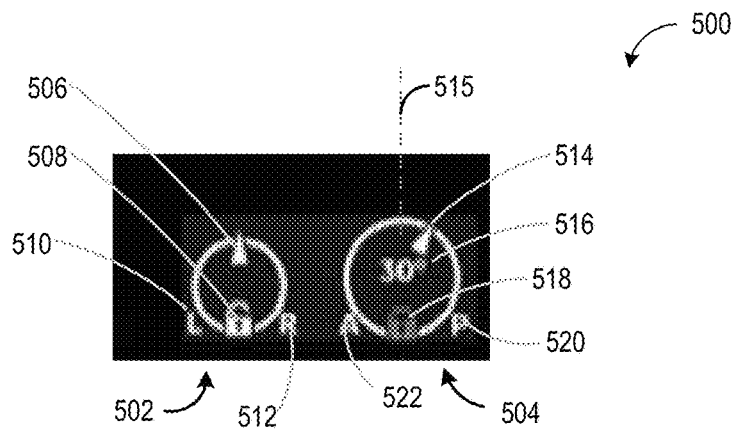
FIG. 5A shows an example user interface element indicating a position of control wheels of a handheld ultrasound device.

Turning to FIG. 4A, a first embodiment of a graphical UI 400 of an ultrasound imaging (e.g., the UI 115 of the ultrasound imaging system 100 of FIG. 1) system is shown. UI 400 may be displayed on a display device of the ultrasound imaging system during operation of a TEE ultrasound device (e.g., the handheld ultrasound device 200 of FIG. 2A) during an examination of patient by an operator.

UI 400 may comprise various display panels, including an ultrasound image panel 402. The ultrasound image panel 402 may include an ultrasound image 404 acquired by a probe of the ultrasound imaging system, which may update as an operator manipulates the TEE ultrasound device by a handle of the TEE ultrasound device (e.g., the TEE control handle 220 of FIG. 2A). For example, as the operator advances or withdraws a probe of the TEE ultrasound device, a lens/transducer of the probe may move such that a view of one or more anatomical features being scanned by the lens/transducer may change. As the view of the one or more anatomical features being scanned changes, the ultrasound image 404 may be updated. In one example, the probe scans the patient in real time, whereby the ultrasound image 404 is updated in accordance with a frame rate of the TEE ultrasound device (e.g., 7-20 frames per second).

The ultrasound image panel 402 may include additional information. For example, the ultrasound image panel 402 may include an electrocardiogram (EKG) graph 416, which may indicate a strength and timing of a heartbeat of the patient. The ultrasound image panel 402 may also include a textual information display 406, comprising information such as a duration of the examination, frame rate per second, scan frequency, scan depth, and so forth, which may be updated by the operator as the probe moves and/or as time passes. An informational panel 408 may also include additional, similar, and/or other textual or graphical information. In one example, the informational panel 408 displays one or more settings and/or parameters of the ultrasound imaging system. For example, informational panel 408 may display the frame rate per second, scan frequency, scan depth, dB power, dB gain, Scan depth in cm and so forth.

The UI 400 may include an image store panel 410, which may display one or more selected images, such as an example selected ultrasound image 412. Over a course of the examination, the operator may wish to capture and save one or more ultrasound images (e.g., frames) for later reference. For example, the operator may detect an abnormality in an anatomical feature of the patient, such as a growth, or damage to the anatomical feature, and may wish to save an image of the abnormality to include in a file of the patient, and/or to discuss treatment options with the patient, and/or for consultation with a specialist, and/or for a different reason. In one example, the operator captures and stores an ultrasound image via a selection button on the handle of the TEE ultrasound device (e.g., the second, selection button 304 of FIGS. 3A and 3B). For example, when the operator encounters an ultrasound image that the operator wishes to save, the operator may select the selection button with a thumb (e.g., the thumb 324 of FIG. 3B) to save the ultrasound image to the image store. When the ultrasound image is saved to the image store, the ultrasound image may appear as a thumbnail image within the image store panel 410, as shown by the example selected ultrasound image 412. In another example, a double-click functionality may be used to select the ultrasound image. For example, the operator may press the selection button a first time to select the ultrasound image (e.g., a current frame in the ultrasound image panel 402), which may freeze the image on the screen, and may press the selection button a second time to save the image to the image store.

The UI 400 may include a control wheel panel 414, which may provide a graphical indication of a rotational position and/or orientation of one or more control wheels on the handle of the TEE ultrasound device (e.g., the first control wheel 202 and the second control wheel 204 of the handheld ultrasound device 200 of FIG. 2A). For example, as the operator manipulates the one or more control wheels as described above in reference to FIG. 2A, the probe of the TEE ultrasound device may flex in one or more planes of freedom via an articulated neck assembly (e.g., the articulated neck assembly 232 of the handheld ultrasound device 200 of FIG. 2A), to allow the operator to advance the probe with minimal damage to soft tissues of the esophagus and/or tilt the probe to facilitate an acquisition of the ultrasound images. As an orientation of the probe relative to an insertion tube of the TEE ultrasound device is adjusted in accordance with a rotation of the one or more control wheels, the control wheel panel 414 may update a graphical representation of the one or more control wheels to indicate the rotation position of the one or more control wheels. Further, the control wheel panel 414 may include an indication of whether one or more of the one or more control wheels is locked. The control wheel panel 414 is described in greater detail below in reference to FIGS. 5A-5E and FIG. 8.

In some examples, the UI 400 may additionally include a virtual track ball interface 418, which is described below in reference to FIG. 4C.

The UI 400 may include a shortcut panel 420, which may include one or more shortcut control elements (also referred to herein as shortcut controls) that may be accessed via one or more buttons arranged on the handle of the TEE ultrasound device (e.g., the first button 302, second button 304, and the third button 306 of the first example configuration of the set of controls 300 of FIG. 3A). In one example, each shortcut element of the one or more shortcut controls duplicates an existing functionality of the ultrasound imaging system (e.g., available via a menu of the ultrasound imaging system), whereby the one or more buttons of the TEE control handle allow the operator an easier and quicker way of accessing the existing functionality. Further, accessing the existing functionality via a menu may involve using a separate input device (e.g., a mouse, touchpad, etc.), which may entail using a non-dominant hand, or taking a hand off of the TEE control handle to manipulate the separate input device, which may be cumbersome and/or distract the operator from a performance of the examination.

In the depicted example, the shortcut panel 420 includes an example shortcut selection with an angle shortcut 422, a store shortcut 424, a 2-D mode shortcut 426, and a color mode shortcut 428. In other examples, the shortcut selection includes additional shortcuts, or a smaller number of shortcuts. The shortcut selection may be configured prior to the examination to include a number of functionalities desired by the operator, where some operators may desire a larger number of functionalities and corresponding shortcuts, and other operators may desire a smaller number of functionalities and corresponding shortcuts. The shortcuts may correspond to modes of operation of the ultrasound system (e.g., 2D mode, 3D mode, 4D mode, color mode, etc.), where selecting a shortcut associated with a mode switches from a current mode of operation to a selected mode of operation. The shortcuts may also correspond to parameters or settings of the ultrasound imaging system. In some examples, selecting a shortcut associated with a parameter or setting of the ultrasound imaging system toggles the parameter between two parameter values or settings of the ultrasound imaging system. In other examples, selecting a shortcut associated with a parameter or setting of the ultrasound imaging system may adjust the parameter or setting by a predetermined value. For example, selecting the angle shortcut 422 may increase or decrease a divergence angle of a lens of the probe by a predetermined angle (e.g., 1°, 5°, 45° or 90° etc. at the operator's preference). In still other examples, selecting a shortcut associated with a parameter or setting of the ultrasound imaging system may transfer a focus of the UI 400 to a different set of control elements to set or reset the parameter or setting. For example, selecting a shortcut associated with a parameter or setting may pop up a window of the UI 400 wherein the operator may select or enter in a new parameter value or setting, or may transfer focus to another panel of the UI 400 (e.g., the virtual trackball interface panel 418) wherein the operator may select or enter in a new parameter value or setting. The shortcuts may also correspond to permitted actions of the ultrasound system. For example, selecting the store shortcut 424 may store a current ultrasound image 404 to the image store.

In one example, the operator navigates between shortcuts of the shortcut panel 420 by pressing the one or more buttons on the handle of the TEE ultrasound device to advance a focus of the UI 400 forward or backward through the shortcut selection to select a desired shortcut of the shortcut selection, as indicated by the forward arrow 432 and the back arrow 430, respectively. For example, one of the one or more buttons may be a forward directional button (e.g., the third, forward button 306 of FIG. 3A), which may allow the operator to advance forward through the shortcut selection, and a different one of the one or more buttons may be a backward directional button (e.g., the first, back button 302 of FIG. 3A), which may allow the operator to advance in a reverse direction through the shortcut selection. Yet another button of the one or more buttons may be a selection button (e.g., the second, selection button 304 of FIG. 3A), which may allow the operator to select a shortcut from the shortcut selection. Thus, if the focus of the UI 400 is on the angle shortcut 422 (e.g., a default focus due to a position of the angle shortcut 422, or a previous focus from an earlier selection, etc.), the operator may press the forward directional button once to advance the focus to in a forward direction (e.g., to a right-hand side of the operator) to the store shortcut 424. As the focus advances in the forward direction, a first visual indication may be provided in the UI 400 to indicate a current location of the focus (e.g., illumination, backlighting, outlining, or other form of highlighting). The operator may press the forward directional button a second time to advance the focus in the forward direction to the 2-D mode shortcut 426. If the operator desires to switch to a 2D mode of operation, the operator may select the 2D mode of operation by pressing the selection button while the focus is on the 2D mode shortcut 426. Alternatively, if the focus of the UI 400 is on the color mode shortcut 428, the operator may press the backward directional button once to advance the focus in a backward direction (e.g., to a left-hand side of the operator) to the 2D mode shortcut 426, where the operator may select the 2D mode shortcut 426. When the 2D mode of operation is selected, a second visual indication may be provided in the UI 400 to indicate a selection of the 2D mode (e.g., illumination, backlighting, outlining, or other form of highlighting). In some examples, the focus of the UI 400 may be maintained from a last selection of the operator and indicated to the operator (e.g., to show a current mode of operation), while in other examples an indication of the focus may not be maintained (e.g., after changing a setting or parameter, saving an image, etc.). In one example, when the 2D mode is selected, the 2D mode shortcut 426 changes to indicate a 4D mode shortcut, so that the user can use the same button to switch from the 2D mode to 4D mode.

In one example, a limited number of shortcut controls are displayed in the shortcut panel 420, where the limited number of shortcut controls is a number of shortcut controls that may be visible in the shortcut panel 420 at one time. In other examples, a larger number of shortcut controls may be displayed in shortcut panel 420, where some shortcut controls of the selection of shortcut controls are visible and one or more shortcut controls of the selection are not visible. For example, when navigating through the shortcut controls of the selection via the forward directional button in the direction of the forward arrow 432, as the operator navigates to a right side of the shortcut panel 420, an additional shortcut element that was not visible may appear at the right side of the shortcut panel 420, while the visible shortcut controls may shift in a left direction indicated by the back arrow 430, with the visible shortcut element on the left side of the shortcut panel 420 disappearing from view. Alternatively, when navigating through the shortcut controls of the selection via the back directional button in the direction of the back arrow 430, as the operator navigates to a left side of the shortcut panel 420, an additional shortcut element that was not visible may appear at the left side of the shortcut panel 420, while the visible shortcut controls may shift in a right direction indicated by the forward arrow 432, with the visible shortcut element on the right side of the shortcut panel 420 disappearing from view. In this way, a number of shortcut controls may be permitted that exceeds the number of shortcut controls that may be visible in the shortcut panel 420 at one time, and the operator may scroll through the shortcut controls using the one or more buttons on the control handle.

As an example, the operator may be acquiring images of a heart of a patient in a 2D mode of operation of the ultrasound imaging system, and may wish to switch to a color mode of operation of the ultrasound imaging system. The operator may not wish to put a TEE control handle down in order to switch from the 2D mode of operation to the color mode of operation using a menu of the ultrasound imaging system, as putting the TEE control handle down may cause an unintended adjustment of a position and/or orientation of the probe, resulting in a change in the ultrasound images generated in the ultrasound image display panel 402. The operator may also not wish to use a left hand to manipulate a mouse to open the menu, because a button configuration of the mouse is configured for use by a right hand and not a left hand, making it awkward to select an appropriate button of the mouse. As a result of not wishing to put the TEE control handle down and not wishing to use the left hand to open the menu with the mouse, the operator may use one or more buttons of the TEE control handle to switch from the 2D mode to the color mode. To switch from the 2D mode to the color mode, the operator may press the forward directional button and/or the back directional button to navigate between the shortcut controls of the shortcut panel 420 (e.g., depending on a default position or currently selected shortcut element). As the operator navigates from one shortcut element to a next shortcut element via the forward directional button and/or a back directional button, a location of the focus is highlighted (illuminated, backlit, outlined, etc.) in a first highlighting manner. When the operator navigates to the color mode shortcut 428 (e.g., indicating a switch to a color mode of operation of the ultrasound imaging system), the operator may press the selection button on the TEE control handle to select the color mode shortcut 428. When the color mode shortcut 428 is selected by the operator, the location of the focus is highlighted (illuminated, backlit, outlined, etc.) in a second highlighting manner to indicate a selection of the shortcut at the location of the focus (e.g., the color mode shortcut 428). Concurrently, the ultrasound imaging system switches from the 2D mode of operation to the color mode of operation. By using the one or more buttons of the TEE control handle to switch from the 2D mode to the color mode, the operator may maintain a visual focus on the UI 400 during a transition from the 2D mode to the color mode, thereby facilitating a faster and smoother examination.

The one or more of the one or more buttons on the handle of the TEE ultrasound device may be further configured to perform a function when selected in rapid succession, or when selected in a predetermined pattern. In one example, the selection button may be configured to perform an action when double-clicked, such as capturing and storing a current ultrasound image 404 in the image store. As another example, the selection button may be configured to toggle between two states of the ultrasound imaging system when double-clicked (e.g., two modes of operation, two alternative parameter settings, etc.). For example, the operator may wish to compare in a repeated, back-and-forth manner, ultrasound images acquired during a 2D mode of operation with ultrasound images acquired during a 4D mode of operation, or ultrasound images acquired in accordance with a first set of parameters against ultrasound images acquired in accordance with a second set of parameters.

In other examples, the handle of the TEE ultrasound device may not include a plurality of buttons, and may include an alternative set of controls for navigating within the shortcut panel 420, as described below in reference to FIG. 3C.

Turning now to FIG. 3C, a TEE control handle view 350 shows a second example configuration of a set of controls 352 for interacting with a UI of an ultrasound imaging system via a TEE control handle 360. The ultrasound imaging system may be a non-limiting example of the ultrasound imaging system 200 of FIG. 28, and the TEE control handle 360 may be a non-limiting example of the TEE control handle 220 of FIG. 2A. In accordance with one embodiment, the second example configuration of the set of controls 352 includes a selection button 356 positioned within a circular, radial touchpad 354 arranged on a side of the TEE control handle 360, below a first control wheel 314 (e.g., the first control wheel 202 of FIG. 2A), a second control wheel 316 (e.g., the second control wheel 204 of FIG. 2A), and a control wheel lock 318 (e.g., the control wheel lock 206 of FIG. 2A), where the first control wheel 314, the second control wheel 316, and the control wheel lock 318 are coaxially arranged on a top side of the TEE control handle 360. In one example, the selection button 356 (labeled in FIG. 3C with the text "OK") is used to indicate a user selection in the UI of the ultrasound imaging system, and the radial touchpad 354 is used to scroll through one or more control elements in a display panel of the UI (e.g., the shortcut selection of the shortcut display panel 420 of FIG. 4A). When the TEE control handle 360 is being used by an operator, the TEE control handle 360 may be held by the operator with a bottom surface 358 of the TEE control handle against a palm of the operator, such that the selection button 356 and the radial touchpad 354 of the second example configuration of the set of controls 352 may be manipulated by a thumb of the operator.

While the example set of controls 352 of FIG. 3C includes the radial touchpad 354, in one example, the radial touchpad 354 is substituted with a one-axis or single axis touchpad (not depicted in FIG. 3C), where the operator may perform a drag operation with a finger or thumb across the one-axis touchpad (e.g., along the single axis of the touchpad) to scroll through the one or more control elements in the display panel of the UI. An advantage of using a one-axis touchpad rather than the radial touchpad 354 is that an amount of space occupied by the set of controls 352 may be reduced, allowing for a use and/or a greater ease of operation with a TEE control handle of a smaller size. Thus, it should be appreciated that for examples where the one-axis touchpad replaces the radial touchpad 354, as described herein, scrolling the radial touchpad 354 in a first rotational direction and/or a second, opposite rotational direction (e.g., opposite the first rotational direction) may be functionally equivalent to scrolling the one-axis touchpad in a first axial direction and/or a second, opposite axial direction, whereby references to scrolling via the radial touchpad 354 (e.g., dragging a thumb along the radial touchpad 354) in a first rotational direction and/or a second, opposite rotational direction may be replaced by references to scrolling the one-axis touchpad in the first axial direction and/or the second, opposite axial direction.

Referring briefly to FIG. 3D, a view 370 of the second example configuration of the set of controls 352 shows an orientation of the selection button 356 and the radial touchpad 354 when the TEE control handle 360 is being used by an operator, where a hand 372 of the operator grips the TEE control handle 360 with the palm of the operator against the bottom surface 358 of the TEE control handle 360. When holding the TEE control handle 360 as shown in the view 370, a thumb 374 of the operator may be positioned above the second example configuration of the set of controls 352, where the selection button 356 and the radial touchpad 354 are within a comfortable range of the thumb 374.

The selection button 356 and the radial touchpad 354 may be functionally mapped to one or more actions in a user interface of the ultrasound imaging system, as described below in reference to FIG. 4B.

Figure 4B:
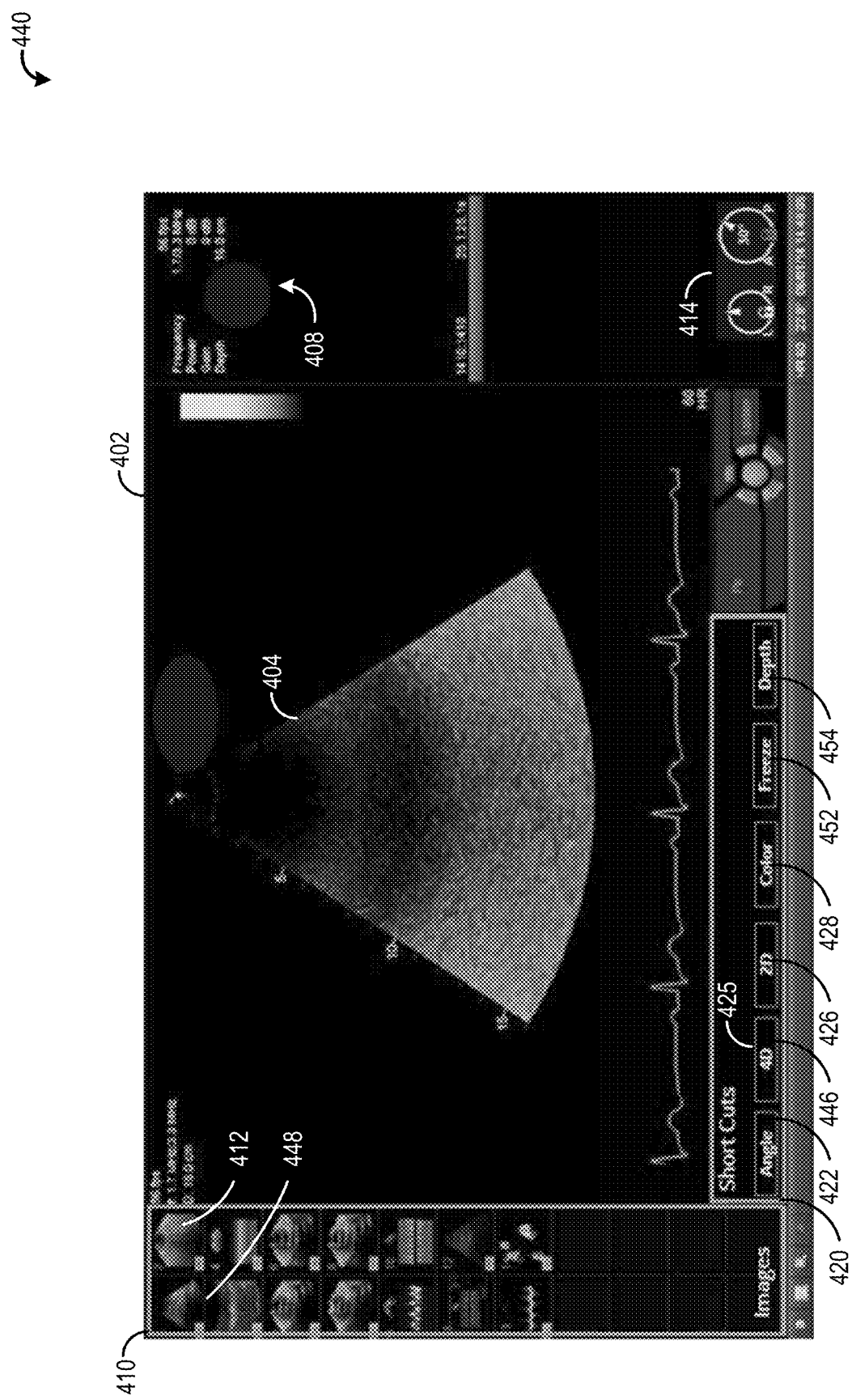
FIG. 4B shows an example user interface of an ultrasound system in a second configuration.
Figure 4C:
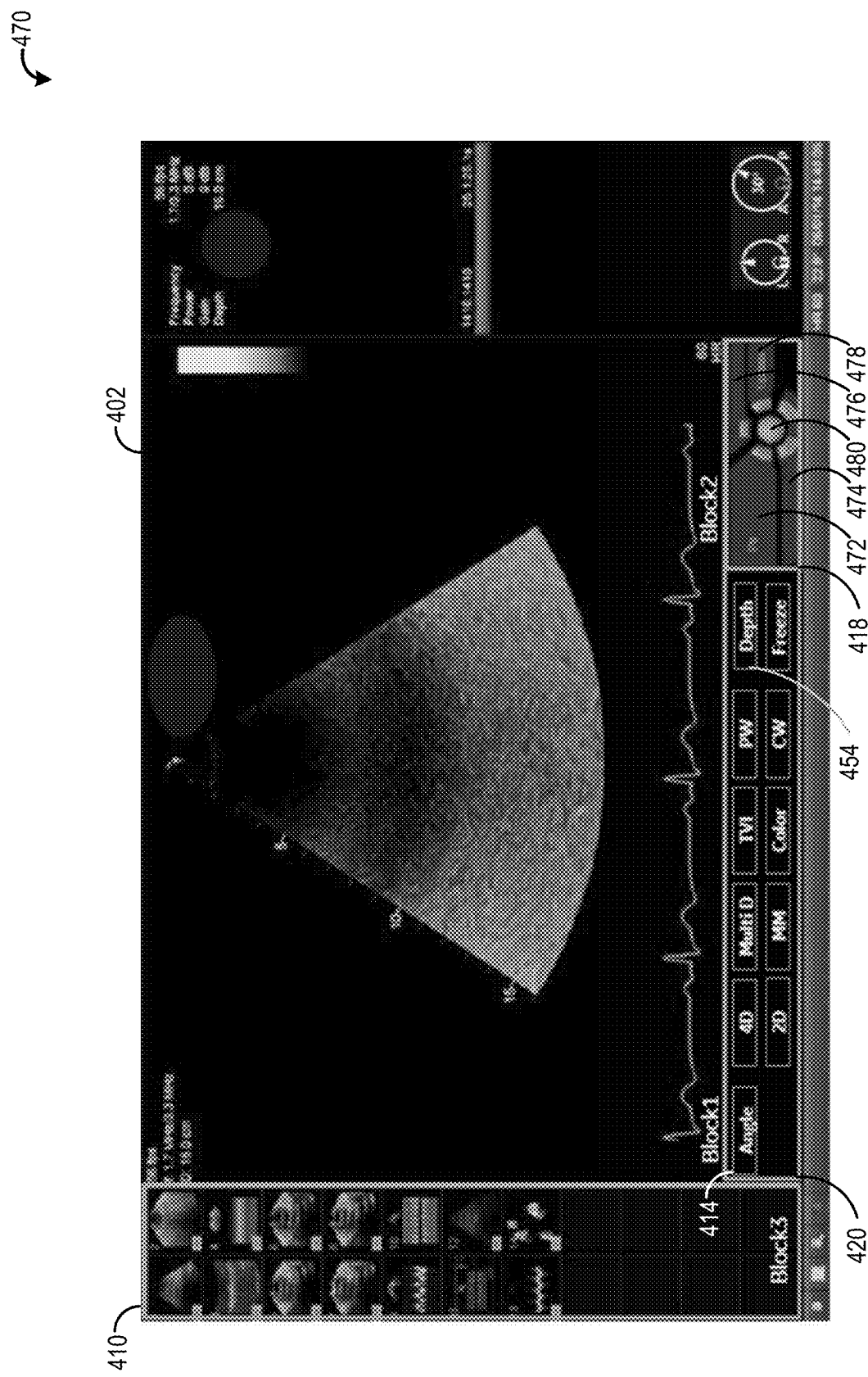
FIG. 4C shows an example user interface of an ultrasound system in a third configuration.

Turning to FIG. 4B, a second embodiment 440 of the graphical UI 400 of FIG. 4A is shown, including the ultrasound image panel 402, the informational panel 408, the control wheel panel 414, the image store panel 410, and the shortcut panel 420. In the second embodiment 440, the shortcut panel 420 includes an expanded selection of shortcut display elements over FIG. 4A, where in addition to the angle shortcut 422, the 2D mode shortcut 426, and the color mode shortcut 428, a 4D mode shortcut 446, a freeze shortcut 452, and a depth shortcut 454 are added. While a forward arrow and a back arrow are not depicted in FIG. 4B, it should be appreciated that other embodiments may include the forward arrow and the back arrow, and/or similar graphical elements.

In the depicted embodiment, an operator of the ultrasound imaging system may use one or more controls on a TEE control handle (e.g., the first example configuration of the set of controls 300 of FIG. 3A) to navigate through one or more control or display elements within a panel of the graphical UI 440 (e.g., the shortcut panel 420 or the image store panel 410), and the operator may also use the one or more controls on the TEE control handle to navigate (e.g., to toggle) between the shortcut panel 420 and the image store panel 410. In one example, the operator uses a forward directional button (e.g., the third, forward button 306 of FIG. 3A) to scroll through the one or more shortcuts within the shortcut panel 420 or to scroll through a plurality of images in the image store panel 410, and the operator may use a back directional button (e.g., the first, back button 302 of FIG. 3A) to navigate between the shortcut panel 420 and the image store panel 410.

For example, the operator may wish to scroll to the right across the shortcut panel 420 to select the 4D mode shortcut 446. A focus of the UI may initially be on the angle shortcut 422 (e.g., by default, upon initiation, etc.). By selecting the forward directional button, the focus may shift to the 4D mode shortcut 446, whereby an outline 425 of the 4D mode shortcut 446 may be illuminated to indicate the location of the focus. The operator may press a selection button (e.g., the second, selection button 304 of FIG. 3A) on the TEE control handle to select the 4D mode shortcut 446, whereby the ultrasound imaging system may switch from a current mode, or a default mode, of the ultrasound imaging system to the 4D mode. A color, illumination, or other visual property of the 4D mode shortcut may be altered to indicate that the 4D mode has been selected. While operating in the 4D mode, the operator may save an ultrasound image 404 to an image store by double-clicking the selection button, whereby the ultrasound image thumbnail 412 may appear in the image store panel 410. If the operator wishes to view the saved ultrasound image 404 in the image store, the operator may select the back directional button, thereby transferring the focus to the image store panel 410. Upon the focus transferring to the image store panel, the focus may be placed on a default thumbnail 448 (e.g., an image positioned at a top left side of the image store panel 410) by default. To view the saved ultrasound image 404, the operator may navigate (e.g., scroll) to the right to the ultrasound image thumbnail 412 by selecting the forward directional button. When the focus is on the image thumbnail 412, the operator may select the image thumbnail 412 by pressing the selection button, which may cause the saved ultrasound image 404 to be displayed in the ultrasound image panel 402. If the operator then wishes to adjust an angle of deflection of the probe, the operator may navigate (e.g., toggle) back to the short cut panel 420 by selecting the back directional button, which may transfer the focus to the 4D mode shortcut 446 of the shortcut panel 420 (e.g., a current or previously selected mode). To navigate to the angle shortcut 422, the operator may scroll (e.g., shift the focus) towards the right side of the shortcut panel 420 by selecting the forward directional button a first time to position the focus on the 2D mode shortcut 426, a second time to position the focus on the Color mode shortcut 428, a third time to position the focus on the Freeze shortcut 452, a fourth time to position the focus on the Depth shortcut 454, and a fifth time to cycle back to the angle shortcut 422 (e.g, due to the back directional button being used to navigate between the shortcut panel 420 and the image store 410). In this way, the operator may use the forward directional button, the back directional button, and the selection button to navigate within or between the shortcut panel 420 and the image store 410.

In another example, the one or more controls on the TEE control handle may not include the forward directional button and the back directional button (e.g., the first example configuration of the set of controls 300 of FIG. 3A), and the one or more controls on the TEE control handle may include a radial touchpad and the selection button (e.g., the radial touchpad 354 and the selection button 356 of the second example configuration of the set of controls 352 of FIG. 3C). The operator may use the radial touchpad to scroll through the one or more shortcuts within the shortcut panel 420 or to scroll through a plurality of images in the image store panel 410. For example, the operator may drag a thumb (or a finger) in a first rotational direction (e.g., a clockwise direction, or a counter-clockwise direction) around the radial touchpad to scroll through the one or more shortcut controls of the shortcut panel 420 and/or the plurality of images in the image store panel 410, and the operator may drag the thumb (or the finger) in a second, opposite rotational direction around the radial touchpad to navigate between the shortcut panel 420 and the image store panel 410.

Further, the radial touchpad may be used to navigate between additional panels of the graphical UI 400 (e.g., other panels in addition to the image store panel 410 and the shortcut panel 420). For example, FIG. 4C shows a third embodiment 470 of the graphical UI 400 of FIG. 4A with three display panels that the operator may navigate between, the shortcut panel 420 (labeled as Block 1), the virtual track ball interface 418 (labeled as Block 2), and the image store panel 410 (labeled as Block 3). In one example, the operator drags the thumb (or the finger) in a first rotational direction (e.g., clockwise or counter-clockwise) around the radial touchpad to navigate between the shortcut panel 420, the virtual track ball interface 418, and the image store panel 410 in the first direction, and the operator drags the thumb (or the finger) in a second, opposite rotational direction (e.g., counter-clockwise or clockwise) around the radial touchpad to navigate between control elements displayed within the shortcut panel 420, the virtual track ball interface 418, and the image store panel 410, in the second direction.

For example, in the third embodiment 470, the shortcut panel 420 includes an expanded selection of shortcut controls over FIG. 4B, where the expanded selection of shortcut controls is displayed in a plurality of rows. In one example, the operator may scroll through the expanded selection of shortcut controls using the radial touchpad in a cyclical manner, where dragging the thumb or finger around the radial touchpad in the second, opposite rotational direction may shift the focus of the graphical UI 400 in the second, opposite rotational direction through the selection of shortcut controls. For example, the operator may drag the thumb around the radial touchpad in the second, opposite rotational direction, which may cause the focus of the UI to shift in the second, opposite rotational direction through the selection of shortcut controls, starting from a shortcut control with a default focus. If the operator wishes to shift the focus to the image store panel 410 or the virtual track ball interface 418, the operator may drag the thumb around the radial touchpad in the first rotational direction, which may cause the focus of the UI to shift in the first rotational direction through the image store panel 410 or the virtual track ball interface 418 (e.g., if the first rotational direction is clockwise, the focus is shifted to the image store panel 410 and then to the virtual track ball interface 418, and if the first rotational direction is counter-clockwise, the focus is shifted to the virtual track ball interface 418 and then to the image store panel 410).

The virtual track ball interface 418 may include a first button 472, a second button 474, a third button 476, and a fourth button 478 arranged around a center point 480. The first, second, third, and fourth buttons 472, 474, 476, and 478 may be control elements that are mapped to additional functionalities, settings, parameters, actions, and so forth, of the ultrasound imaging system. In one example, the first, second, third, and fourth buttons 472, 474, 476, and 478 are control elements that correspond to functionalities available via a physical track ball interface of the ultrasound imaging system, where the operator may access the functionalities by adjusting the focus of the ultrasound imaging system to a desired button of the first, second, third, and fourth buttons 472, 474, 476, and 478 by performing a drag operation around the radial touchpad in the second, opposite rotational direction, as described above, and selecting the desired button of the first, second, third, and fourth buttons 472, 474, 476, and 478 via the selection button. By using the virtual track ball interface 418 to access the functionalities available via a physical track ball interface, the operator may access the functionalities more efficiently. For example, the physical track ball interface may be located relatively far from the operator during the ultrasound examination, or the physical track ball interface may be ergonomically difficult to manipulate during the ultrasound examination (e.g., due to cramped space, etc.). An additional advantage of accessing the functionalities available via the virtual track ball interface 418 is that a risk of cross contamination may be reduced due to the operator not touching the physical track ball interface.

In another example, the operator may use the virtual track ball interface 418 to adjust one or more settings of a parameter of the ultrasound imaging system selected in the shortcut panel 420. For example, to adjust a depth parameter of the probe, the operator may drag the thumb around the radial touchpad in the first rotational direction to position the focus of the UI on the shortcut panel 420, and may drag the thumb around the radial touchpad in the second, opposite rotational direction to position the focus of the UI on the Depth shortcut control 454. In one example, the operator may use the selection button to select the shortcut panel 420, while in other examples, the operator may not use the selection button to select the shortcut panel 420, and may select the shortcut panel 420 by switching from dragging the thumb around the radial touchpad in the first rotational direction to dragging the thumb around the radial touchpad in the second, opposite rotational direction. When the focus is on the Depth shortcut control 454, the operator may select the Depth shortcut control 454 by pressing the selection button. When the selection button is pressed, the Depth shortcut control 454 may be illuminated to indicate that the Depth shortcut control 454 has been selected. When the Depth shortcut control 454 is selected, a first depth setting of the depth parameter may be displayed in the first rotational element 472, a second depth setting of the depth parameter may be displayed in the second rotational element 474, a third depth setting of the depth parameter may be displayed in the third rotational element 476, and a fourth depth setting of the depth parameter may be displayed in the fourth rotational element 478. The operator may shift the focus of the graphical UI 400 to the virtual track ball interface 418 by dragging the thumb around the radial touchpad in the second, opposite rotational direction, and the operator may navigate between the first rotational element 472, the second rotational element 474, the third rotational element 476, and the fourth rotational element 478 by dragging the thumb around the radial touchpad in the first rotational direction, and select the appropriate depth setting of the depth parameter by pressing the selection button. In this way, the operator may use the controls on the TEE control handle to adjust a setting of a parameter of the ultrasound imaging system without using a separate input device (e.g., a mouse, a track ball, etc.) and while maintaining an attention of the operator on the ultrasound images displayed in the ultrasound image panel 402.

It should be appreciated that the examples provided herein are for illustrative purposes and are non-limiting, where other buttons, touchpads, or similar controls of the TEE control handle may be combined, used interchangeably or substituted to direct the focus of the graphical UI 400 between and within display panels of the graphical UI 400.

Referring now to FIG. 5A, an example graphical control wheel display element 500 is shown that indicates a rotational position of a first control wheel and a rotational position of a second control wheel, and a state of a control wheel lock, of a TEE control handle of an ultrasound imaging system (e.g., the first control wheel 202, the second control wheel 204, and the control wheel lock 206 of the handheld ultrasound device of FIG. 2A). The graphical control wheel display element 500 may be displayed in the UI 400, for example, in the control wheel display panel 414 of FIGS. 4A, 4B, and 4C. As an operator of the TEE control handle manipulates the first control wheel and the second control wheel, a probe coupled to the TEE control handle may flex or tilt in one or more planes of freedom via an articulated neck assembly (e.g., the articulated neck assembly 232 of the handheld ultrasound device 200 of FIG. 2A), and as a position and an orientation of the probe relative to an insertion tube of the TEE ultrasound device is adjusted in accordance with a rotation of the first control wheel and the second control wheel, the graphical control wheel display element 500 may update a graphical representation of the first control wheel and the second control wheel to indicate the rotation of the first control wheel and the second control wheel.

The graphical control wheel display element 500 may include a first graphical control wheel display 502, which shows a rotational position of the first control wheel of the TEE control handle, and may include a second graphical control wheel display 504, which shows a rotational position of the second control wheel of the TEE control handle. In one example, the first graphical control wheel display 502 and the second graphical control wheel display 504 may have a difference in size based on a difference in size between the first control wheel and the second control wheel. For example, if the first control wheel has a smaller diameter than the second control wheel, the first graphical control wheel display 502 may have a smaller diameter than the second graphical control wheel display 504. Alternatively, if the first control wheel has a larger diameter than the second control wheel, the first graphical control wheel display 502 may have a larger diameter than the second graphical control wheel display 504.

In one example, the first control wheel controls a deflection of a probe coupled to the TEE control handle in a first plane of freedom corresponding to a movement of the probe in a left or right direction (e.g., towards a left side of the patient or towards a right side of the patient), which is indicated on the first graphical control wheel display 502 by a left direction indicator 510 and a right direction indicator 512, and the second control wheel controls a deflection of a probe coupled to the TEE control handle in a second plane of freedom corresponding to a movement of the probe in an anterior or posterior direction (e.g., towards a front side of the patient or towards a back side of the patient), which is indicated on the first graphical control wheel display 502 by an anterior direction indicator 522 and a posterior direction indicator 524. While for the purposes of this example, the first control wheel indicates the movement of the probe in the left/right direction and the second control wheel indicates the movement of the probe in the anterior/posterior direction, it should be appreciated that in other examples the first control wheel may indicates the movement of the probe in the anterior/posterior direction and the second control wheel may indicate the movement of the probe in the left/right direction, or the first control wheel and/or the second control wheel may indicate movement in a different dimension without departing from the scope of this disclosure.

The first graphical control wheel display 502 may include a rotational position indicator 506, which may indicate a rotational position of the first control wheel relative to a default, neutral position in which a probe coupled to the TEE control handle has a 0° deflection to the left side of the patient or to the right side of the patient. Similarly, the second graphical control wheel display 504 may include a rotational position indicator 514, which may indicate a rotational position of the second control wheel relative to a default, neutral position (indicated by dashed line 515) in which a probe coupled to the TEE control handle has a 0° deflection towards the front of the patient or towards the back of the patient. For example, the rotational position indicator 514 of the second graphical control wheel display 504 is offset 30° clockwise from the neutral position, as indicated by a text indicator 516 of the second graphical control wheel display 504, indicating that the second control wheel 504 has been rotated 30° from the neutral position.

In the non-limiting example of FIG. 5A, the rotational position indicator 506 is graphically represented by a triangle arrowhead that points in a direction corresponding to the rotational position of the first control wheel relative to the neutral position (e.g., pointing up vertically). The graphical representation of the rotational position indicator may additionally be augmented by a textual representation (e.g., such as the text indicator 516 of the second control wheel 504). Thus, according to the example depicted in FIG. 5A, from the first graphical control wheel display 502 and the second graphical control wheel display 504 it may be inferred that the probe is not deflected toward either the left side or the right side of the patient, and that the probe is deflected from the neutral position by 30° towards the back of the patient.

The first graphical control wheel display 502 may include a lock indicator 508, and the second graphical control wheel display 504 may include a lock indicator 518. The lock indicators 508 and 518 may indicate the state of the control wheel lock of the first control wheel and second control wheel of the TEE control handle. For example, the lock indicator 508 may indicate that the first control wheel is not in a locked state, by displaying an image of an unlocked padlock, while the lock indicator 518 indicate that the second control wheel is in a locked state, by displaying an image of a locked padlock. Further, a locked state may be indicated by a change of color or similar alteration of an appearance of the locked padlock.

Figure 5B:
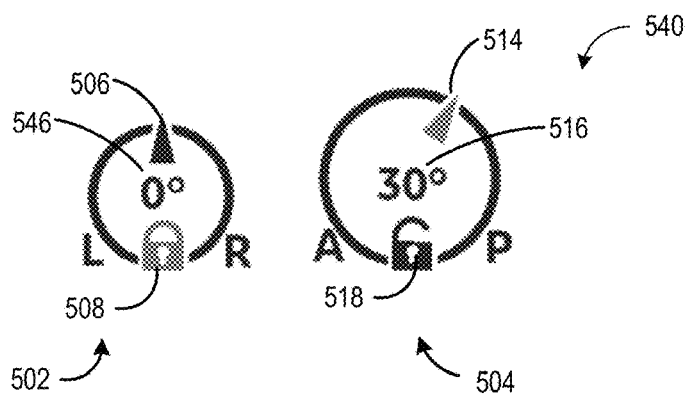
FIG. 5B shows a first example user interface element indicating a position of control wheels of a handheld ultrasound device.

FIG. 5B shows a first alternative configuration 540 of the first graphical control wheel display 502 and the second graphical control wheel display 504, where the lock indicator 508 of the first graphical control wheel display 502 indicates that the first control wheel is in a locked position, while the lock indicator 518 of the second graphical control wheel display 504 indicates that the second control wheel is not in a locked position. In the first alternative configuration 540, the first graphical control wheel display 502 includes a text indicator 546 indicating a degree of rotation of the first control wheel (e.g., 0°), and a corresponding degree of deflection of the probe in the left or the right direction (e.g., 0°). Additionally, the rotational position indicator 506 of the first graphical control wheel display 502 is not highlighted due to the probe being in a neutral, straight position in the first (e.g., left-right) plane of freedom. However, the rotational position indicator 514 of the second graphical control wheel display 504 is highlighted (e.g., via a color change, change in intensity, etc.), indicating that the second control wheel has been rotated 30° from the neutral position. In some examples, the ratio of wheel rotation angle and bend angle may vary from probe to probe.

Figure 5C:
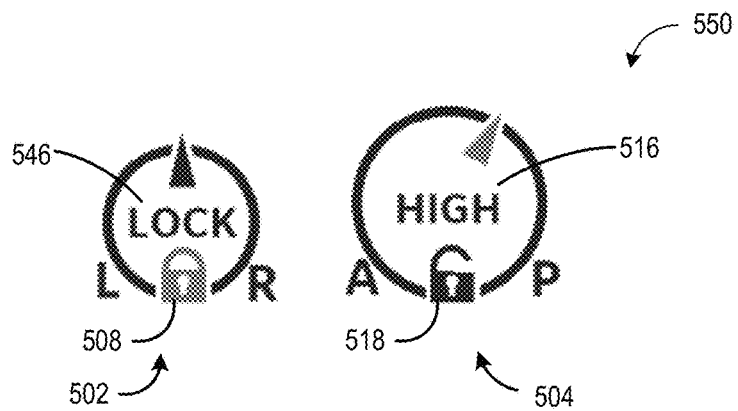
FIG. 5C shows a second example user interface element indicating a position of control wheels of a handheld ultrasound device.

In another example, the text indicator 546 of the first graphical control wheel display 502 and/or text indicator 516 of the second graphical control wheel display 504 may not indicate a degree of rotation of the first control wheel and second control wheel, respectively, and a corresponding degree of deflection of the probe, and may include a different textual indication of one or more states of the first graphical control wheel display 502 and/or the second graphical control wheel display 504. In FIG. 5C, a second alternative configuration 550 of the first graphical control wheel display 502 and the second graphical control wheel display 504 shows the text indicator 546 as including text to indicate that the first control wheel is in a locked state, and shows the text indicator 516 of the second graphical control wheel display 504 as including text to indicate that the degree of deflection of the probe (e.g., at 30°) in the posterior direction is high. In one example, the text indicator 546 includes a textual description of the degree of deflection of the probe in the left or right direction when the first control wheel is unlocked, which changes to a textual description of a state of the control wheel lock when the first control wheel is locked, and the text indicator 516 includes a textual description of the degree of deflection of the probe in the anterior or posterior direction when the second control wheel is unlocked, which changes to a textual description of a state of the control wheel lock when the second control wheel is locked.

Figure 5D:
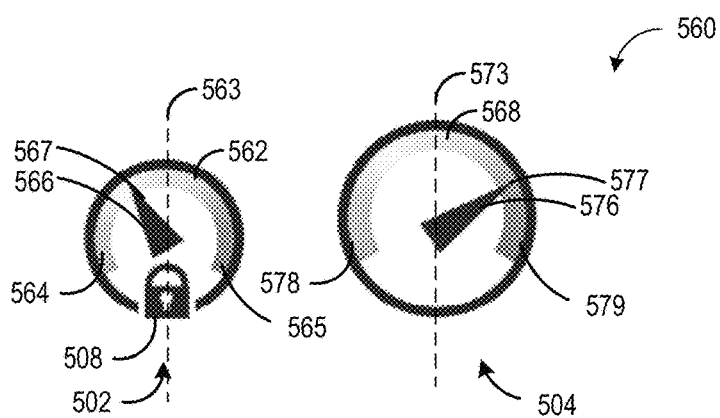
FIG. 5D shows a third example user interface element indicating a position of control wheels of a handheld ultrasound device.

FIG. 5D shows a third alternative configuration of the first graphical control wheel display 502 and the second graphical control wheel display 504, where the rotational position indicator 506 and the text indicator 546 of the first graphical control wheel display 502, and the rotational indicator 514 and the text indicator 516 of the second graphical control wheel display 504 are replaced by a needle indicator configuration. The first graphical control wheel display 502 includes a needle indicator 566, which rotates around a central point of the first graphical control wheel display 502 to indicate a rotational position of the first control wheel, where a degree of deflection of the probe is indicated by an angle of the needle indicator 566 in a clockwise or counterclockwise direction from the neutral point, and by where a point 567 of the needle indicator 566 falls along a color gradient 562. Similarly, the second graphical control wheel display 504 includes a needle indicator 576, which rotates around a central point of the second graphical control wheel display 504 to indicate a rotational position of the second control wheel, where a degree of deflection of the probe is indicated by an angle of the needle indicator 576 in a clockwise or counterclockwise direction from the neutral point, and according to where a point 577 of the needle indicator 576 falls along a color gradient 568. For example, if the needle indicator 566 falls within a light-colored area around the neutral point (indicated by a central line 563), it may be inferred that the degree of deflection of the probe to the right or left side of the patient is low. If the needle indicator 566 falls within a darker-colored area at an extreme end 564 of the color gradient 562 in a counterclockwise direction, it may be inferred that the degree of deflection of the probe towards the left side of the patient is high. Alternatively, if the needle indicator 566 falls within a darker-colored area at an extreme end 565 and of the color gradient 562 in a clockwise direction, it may be inferred that the degree of deflection of the probe towards the right side of the patient is high. Similarly, if the needle indicator 576 falls within a light-colored area around the neutral point (indicated by a central line 573), it may be inferred that the degree of deflection of the probe in an anterior or posterior direction of the patient is low. If the needle indicator 576 falls within a darker-colored area at an extreme end 578 of the color gradient 568 in a counterclockwise direction, it may be inferred that the degree of deflection of the probe in the anterior direction of the patient is high. Alternatively, if the needle indicator 576 falls within a darker-colored area at an extreme end 579 of the color gradient 568 in a clockwise direction, it may be inferred that the degree of deflection of the probe in the posterior direction of the patient is high.

Further, a shading of the color gradients 562 and 568 may indicate one or more desired degree ranges through which the probe may be flexed. For example, a darkness of the shading of the color gradient 562 towards either or both of the extreme ends 564 and 565 may indicate an amount of strain on the articulated neck assembly of the probe in the left or the right direction, respectively, and a darkness of the shading of the color gradient 568 towards either or both of the extreme ends 564 and 565 may indicate an amount of strain on the articulated neck assembly of the probe in the anterior or the posterior direction, respectively. By adjusting a shading of the color gradients 562 and 568, including independently, the operator may be provided visual guidelines for operating the TEE control handle to achieve desired results without putting undue mechanical strain on the probe.

Figure 6:
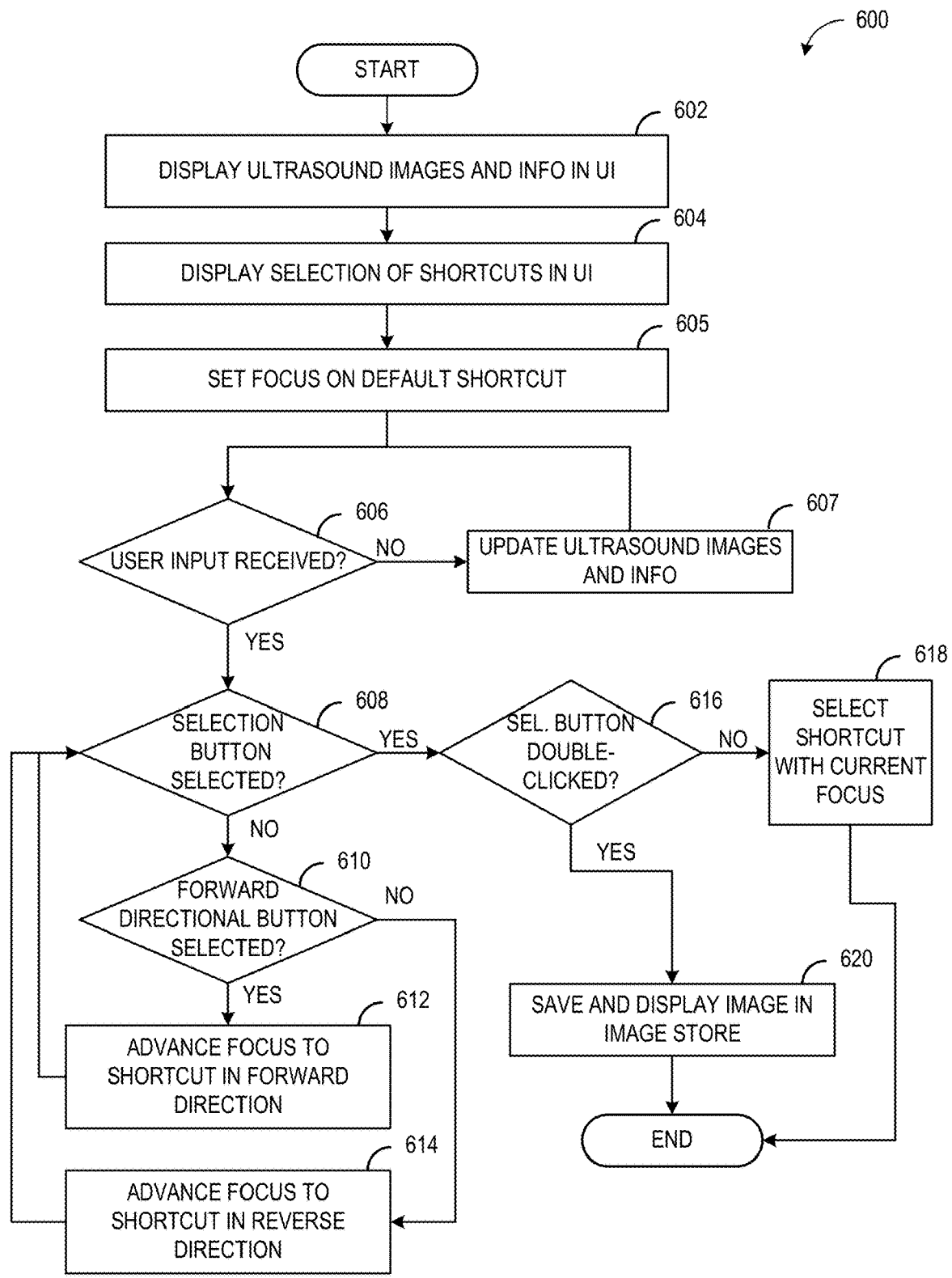
FIG. 6 shows a flowchart illustrating an example method for interacting with a display of a user interface of an ultrasound system via a first configuration of controls.

Referring now to FIG. 6, a flowchart of an exemplary method 600 is shown for interacting with a UI of a medical imaging system, such as the ultrasound imaging system 100 of FIG. 1, via a first configuration of a set of controls of a TEE control handle. The first configuration of the set of controls may include a forward directional button, a back directional button, and a selection button, such as the third button 306, first button 302, and second button 304, respectively, of the first example configuration of the set of controls 300 of FIG. 3A. The TEE control handle may also include a first control wheel and a second control wheel, such as the first control wheel 202 and second control wheel 204 of FIG. 2A. A user interaction with the first control wheel and second control wheel is described below in reference to method 800 of FIG. 8. In an embodiment, operations of method 600 may be stored in non-transitory memory and executed by a processor, such as non-transitory memory 120 and processor 116 of medical imaging system 100 of FIG. 1, respectively, during an ultrasound examination of a patient by an operator of the medical imaging system.

At 602, method 600 includes displaying a medical image and related information on a display device of the medical imaging system (e.g., the display device 118 of medical imaging system 100 of FIG. 1). In one example, the medical image may be an ultrasound image. For example, the medical image may be a 2D, 3D, or 4D ultrasound image, or a Doppler ultrasound image, or any other kind of ultrasound image. In some examples, the medical image may be a single frame of a sequence of medical images acquired from a patient in real time, for example, during an ultrasound examination by a clinician. In other examples, the medical image may be an x-ray image, a CT image, an MRI image, a visible light image, or another type of medical image that includes an anatomical feature of interest.

In one example, the medical image and related information in the UI are displayed as described above in reference to FIG. 4A, where the medical image is generated by a probe arranged at a distal end of an insertion tube coupled to the TEE control handle. As an operator of the medical imaging system begins the examination, the operator may advance the probe into a body cavity of the patient (e.g., an esophagus, etc.) using the TEE control handle. As the probe is advanced into the body cavity, the ultrasound images displayed in the UI may be updated in accordance with a movement of the probe and/or adjustments to a position and/or orientation of the probe made via the first control wheel and second control wheel of the TEE control handle. For example, the operator may advance the probe into the esophagus of the patient towards an ROI of a heart of the patient located behind the esophagus via the TEE control handle. To navigate through one or more curves of the esophagus, as the operator advances the probe into the esophagus, the operator may flex an articulated neck mechanism that couples the probe to the insertion tube to angle the probe to a left or a right side of the patient via the first control wheel, and to angle the probe to a front or a back side of the patent via the second control wheel. When the probe reaches a position in the esophagus proximate the ROI, the operator may adjust a rotational position of the first control wheel and/or the second control wheel to tilt the probe to the left or right and or the front or back of the patient, respectively, to orient a lens of the probe such that an ultrasound beam of the probe deflects off of a target object of the ROI at a perpendicular or close to perpendicular angle to acquire the medical image. The related information may be textual information that is displayed concurrently on the display device, which may include, as a non-limiting list of examples, a frequency of a signal generated by the ultrasound probe, a depth of the ultrasound probe with respect to the ROI, a time passed since a start of the examination, etc.

At 604, method 600 includes displaying a selection of shortcuts (e.g., the shortcut selection described above in reference to FIG. 4A) in the UI. In one example, each shortcut of the selection of shortcuts is associated with a functionality of the medical imaging system. The functionalities associated with the shortcuts may include, for example, switching between modes of operation of the medical imaging system (e.g., between a 2D mode and a 4D mode, or a Doppler mode, or a color mode, etc.); performing actions (e.g., showing, hiding, or expanding a display panel of the UI, freezing a stream of medical images displayed in the UI to view a single frame, capturing and/or storing one or more medical images displayed in the UI in an image store, etc.); setting, resetting, or adjusting parameters or settings of the medical imaging system (e.g., changing a divergence angle of a lens of the probe, adjusting a scan depth in centimeters, scan frequency, frame rate per second, dB power, dB gain of the probe, etc.); displaying additional information and/or graphic elements in the UI (e.g., overlays, reference images, annotations, guidance cues, etc.); and/or other types of functionalities.

In one example, the selection of shortcuts is preconfigured by the operator, or a healthcare organization, prior to the examination. For example, a shortcut functionality may be linked to one or more menu items of the medical imaging system, whereby the operator may add a menu item to the selection, or the selection of shortcuts may be selected from a list of functionalities compiled by a manufacturer of the medical imaging system.

The shortcuts may be displayed as selectable control elements in a shortcut panel of the UI, such as the shortcut panel 420 described above in reference to FIG. 4A-4C. In one example, the shortcut panel is positioned along a bottom edge of the UI, below a display of the ultrasound images, where the shortcuts may be displayed horizontally across the shortcut panel. Displaying the shortcuts may include displaying a name of each shortcut of the selection of shortcuts, or the shortcuts may be represented as graphical control elements (e.g., as buttons) with a shape (e.g., a rectangle, a circle, etc.) that may have an outline. In some examples, the name, shape, and/or outline may be displayed with various degrees of illumination, shading, coloring, etc. to distinguish one shortcut from another shortcut, or to distinguish between a selected shortcut or a shortcut receiving a current focus of the UI. Additionally, an order of the shortcuts in the selection of shortcuts may be configured, for example, extending from a left side of the shortcut panel to a right side of the shortcut panel. For example, the shortcuts may be listed in an order in which the operator selected the shortcuts, or the shortcuts may be listed in an order of frequency of use by the operator or a team of operators. In one example, the operator may configure an order based on a preference of the operator.

At 605, method 600 includes setting a focus of the medical imaging system on a default shortcut. For example, the default shortcut may be a shortcut positioned at a far left position on the shortcut panel (e.g., a first or initial shortcut of the selection of shortcuts), or the default shortcut may be a shortcut most frequently or recently used by the operator or team of operators, which may or may not be in a far left position on the shortcut panel. In one example, the default focus may be indicated to the operator (e.g., by highlighting the name, shape, or outline of the shortcut). In other examples, the default focus may not be indicated to the operator, or the focus may be indicated in response to the operator adjusting the focus via a shortcut button on the TEE control handle.

At 606, method 600 includes determining whether user input has been received via the set of controls of the TEE control handle (e.g., by the operator selecting the forward directional button, the back directional button, or the selection button, but not the first control wheel or the second control wheel). If at 606 it is determined that no user input has been received from the set of controls of the TEE control handle, method 600 proceeds to 607. At 607, method 600 includes updating the ultrasound images generated by the probe and/or any related information in the UI until it is determined that user input has been received. If at 607 it is determined that user input has been received from the set of controls of the TEE control handle, method 600 proceeds to 608.

At 608, method 600 includes determining whether a selection button (e.g., the second, selection button 304 of FIG. 3A) has been selected. If at 608 it is determined that the selection button has not been selected, method 600 proceeds to 610. At 610, method 600 includes determining whether the forward directional button has been selected. If at 610 it is determined that the forward directional button has been selected, method 600 proceeds to 612. At 612, method 600 includes advancing the focus of the UI from a shortcut on which the focus lies to an adjacent shortcut in a forward direction. In one example, the forward direction proceeds from a left side of the UI to a right side of the UI (e.g., the operator's left and right side). If at 610 it is determined that the forward directional button has not been selected, method 600 infers that the back directional button has been selected, where method 600 proceeds to 614. At 614, method 600 includes advancing the focus of the UI from a shortcut on which the focus (referred to herein as the shortcut of focus) lies to an adjacent shortcut in a reverse direction. In one example, the reverse direction proceeds from a right side of the UI to a left side of the UI.

As the focus is advanced in either the forward or the reverse direction, the UI may highlight the shortcut of focus. In one example, highlighting the shortcut of focus lies may include adjusting a color of the shortcut of focus. For example, other shortcuts in the selection of shortcuts may be displayed in a first color, while the shortcut of focus may be displayed in a different, second color. In another example, an illumination of the shortcut of focus may be adjusted (e.g., where the shortcut of focus is illuminated and the other shortcuts in the selection of shortcuts are less illuminated). Alternatively, a visual feature of the shortcut of focus may be adjusted, for example, text of a label of the shortcut may be displayed in bold, or underlined, or more or less illuminated than the other shortcuts in the selection of shortcuts, or a shape or an outline of the shortcut may be adjusted.

If at 608 it is determined that the selection button has been selected, method 600 proceeds to 616. At 616, method 600 includes determining whether the selection button has been double-clicked. If at 616 it is determined that the selection button has not been double-clicked, method 600 proceeds to 618. At 618, method 600 includes selecting the shortcut that is currently the object of the focus (e.g., to execute a functionality associated with the selected shortcut), and method 600 ends. If at 616 it is determined that the selection button has been double-clicked, method 600 proceeds to 620. At 620, method 600 includes saving the medical image displayed in the UI in an image store of the medical imaging system (e.g., for later reference for diagnostic and/or therapeutic reasons, etc.). In one example, an image store panel of the UI (e.g., the image store panel 410 of FIG. 4A) may display thumbnail images of images saved to the image store, whereby when the medical image is saved to the image store, a thumbnail of the medical image appears on the image store panel. Upon saving the medical image to the image store, method 600 ends.

Figure 7:
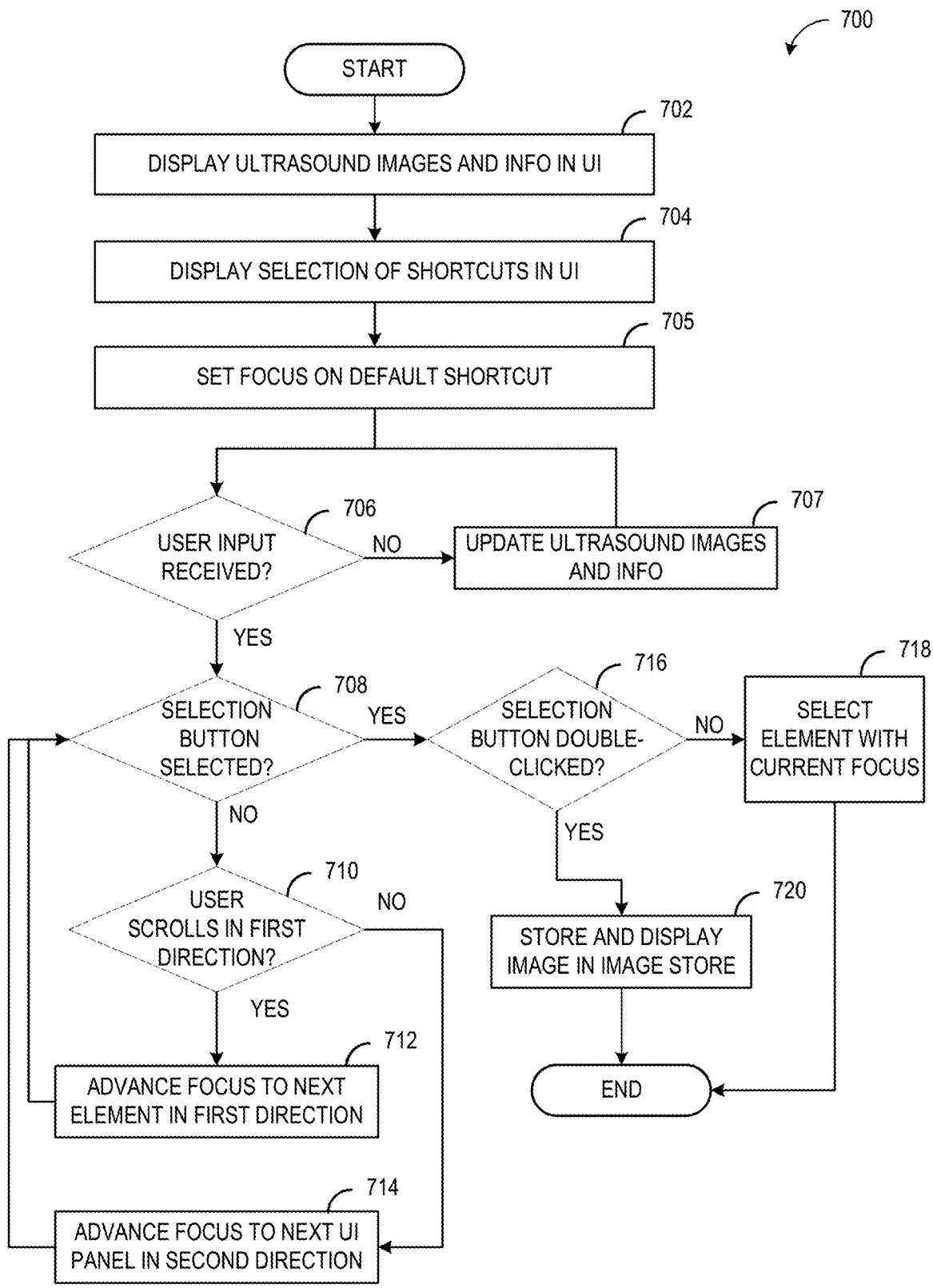
FIG. 7 shows a flowchart illustrating an example method for interacting with a display of a user interface of an ultrasound system via a second configuration of controls.

Referring now to FIG. 7, a flowchart of an exemplary method 700 is shown for interacting with a UI of a medical imaging system, such as the ultrasound imaging system 100 of FIG. 1, via a second configuration of a set of controls of a TEE control handle. The second configuration of the set of controls may not include a forward directional button and a back directional button, and may include a radial touchpad and a selection button, such as the radial touchpad 354 and the selection button 356, respectively, of the second example configuration of the set of controls 352 of FIG. 3C. The TEE control handle may also include a first control wheel and second control wheel, such as the first control wheel 202 and second control wheel 204 of FIG. 2A. In an embodiment, operations of method 700 may be stored in non-transitory memory and executed by a processor, such as non-transitory memory 120 and processor 116 of medical imaging system 100 of FIG. 1, respectively, during an ultrasound examination of a patient by an operator of the medical imaging system.

Steps 702, 704, 705, 706, and 707 of method 700 are identical to the steps 602, 604, 605, 606, and 607 of method 6 described above, where ultrasound images and related information are displayed in the UI described above along with a selection of shortcut control elements in a shortcut panel, an image store panel, and a virtual track ball interface panel, with a focus of the UI being placed on a default shortcut of the shortcut panel. Method 700 updates the ultrasound images and related information until user input is received.

At 708, method 700 includes determining whether a selection button (e.g., the selection button 356 of FIG. 3C) has been selected. If at 708 it is determined that the selection button has not been selected, method 700 proceeds to 710. At 710, method 700 includes determining whether the operator is scrolling in a first rotational direction using the radial touchpad (e.g., by dragging a thumb or finger of the operator around the radial touchpad). If at 710 it is determined that the operator is scrolling in a first rotational direction using the radial touchpad, method 700 proceeds to 712. At 712, method 700 includes advancing the focus of the UI from an element of a panel (e.g., a shortcut in the shortcut panel, a thumbnail in the image store panel, a control element of the virtual track ball interface panel, etc.) on which the focus lies, to an adjacent element of the panel in the first direction. For example, if the operator is scrolling in a clockwise direction using the touchpad while the focus is on a shortcut of the shortcut panel, the focus may advance to an adjacent shortcut of the shortcut panel in the clockwise direction (e.g., from left to right along a single row or a top row of shortcuts of the shortcut panel, and right to left along a bottom row of shortcuts of the shortcut panel).

If at 710 it is determined that the forward directional button has not been selected, method 700 infers that the back directional button has been selected, where method 700 proceeds to 714. At 714, method 700 includes advancing the focus of the UI from the panel on which the focus lies to an adjacent panel in a reverse direction (e.g., an opposite direction from the forward direction). For example, if the operator is scrolling in a counter-clockwise direction using the touchpad while the focus is on a shortcut of the shortcut panel, the focus may advance from the shortcut panel to an adjacent panel in the counter-clockwise direction (e.g., the virtual track ball panel). If the operator continues to scroll in the counter-clockwise direction using the touchpad while the focus is on the virtual track ball panel, the focus may advance from the virtual track ball panel to the image store panel (e.g., the adjacent panel in a counter-clockwise direction). In this way, by using the radial touchpad in one direction (e.g., the first rotational direction), the operator may scroll through control or display elements of the UI arranged within a display panel, and by using the radial touchpad in an opposite direction (e.g., the second, opposite rotational direction), the operator may scroll through display panels of the UI.

If at 708 it is determined that the selection button has been selected, method 700 proceeds to 716. At 716, method 700 includes determining whether the selection button has been double-clicked. If at 716 it is determined that the selection button has not been double-clicked, method 700 proceeds to 718. At 718, method 700 includes selecting the element that is currently the object of the focus (e.g., a shortcut of the shortcut panel, a thumbnail image of the image store panel, or a control element of the virtual track ball panel), and method 700 ends. If at 716 it is determined that the selection button has been double-clicked, method 700 proceeds to 720. At 720, method 700 includes saving the medical image displayed in the UI in the image store of the medical imaging system. Upon saving the medical image to the image store, method 700 ends.

Figure 8:
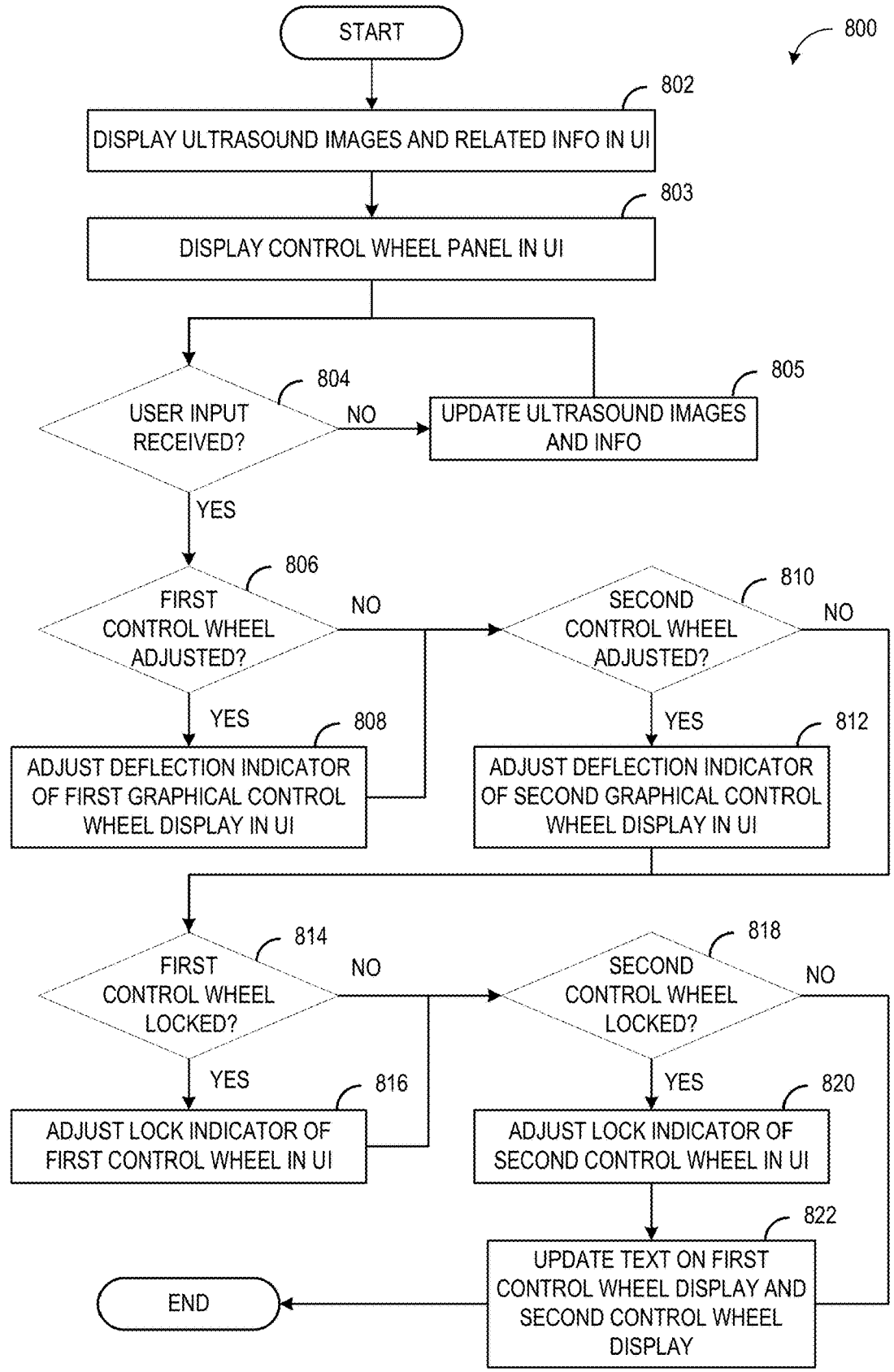
FIG. 8 shows a flowchart illustrating an example method for indicating a status of control wheels of an ultrasound system on a user interface of an ultrasound system.

Referring now to FIG. 8, a flowchart of an exemplary method 800 is shown for interacting with a UI of a medical imaging system, such as the ultrasound imaging system 100 of FIG. 1, via a first control wheel and a second control wheel of a TEE control handle of the medical imaging system, such as the first control wheel 202 and the second control wheel 204 of the handheld ultrasound device 200 of FIG. 2A. In an embodiment, operations of method 800 may be stored in non-transitory memory and executed by a processor, such as non-transitory memory 120 and processor 116 of medical imaging system 100 of FIG. 1, respectively, during an ultrasound examination of a patient by an operator of the medical imaging system.

At 802, method 800 includes displaying a medical image and related information on a display device of the medical imaging system (e.g., the display device 118 of medical imaging system 100 of FIG. 1). In one example, the medical image may be an ultrasound image. For example, the medical image may be a 2D, 3D, or 4D ultrasound image, or a Doppler ultrasound image, or any other kind of ultrasound image. In some examples, the medical image may be a single frame of a sequence of medical images acquired from a patient in real time, for example, during an ultrasound examination by a clinician. In other examples, the medical image may be an x-ray image, a CT image, an MRI image, a visible light image, or another type of medical image that includes an anatomical feature of interest.

In one example, the medical image and related information in the UI are displayed as described above in reference to the graphical UI 400 of FIG. 4A and method 600 of FIG. 6, where the medical image is generated by a probe arranged at a distal end of an insertion tube coupled to the TEE control handle of the medical imaging system. As an operator of the medical imaging system begins the examination, the operator may advance the probe into a body cavity of the patient (e.g., an esophagus, etc.) using the TEE control handle. As the probe is advanced into the body cavity, the ultrasound images displayed in the UI may be updated in accordance with a movement of the probe and/or adjustments to a position and/or orientation of the probe made via the first control wheel and second control wheel of the TEE control handle. For example, the operator may advance the probe into the esophagus of the patient towards an ROI of a heart of the patient located behind the esophagus via the TEE control handle. To navigate through one or more curves of the esophagus, as the operator advances the probe into the esophagus, the operator may flex an articulated neck mechanism that couples the probe to the insertion tube to angle the probe to a left or a right side of the patient via the first control wheel, and to angle the probe to a front or a back side of the patent via the second control wheel. When the probe reaches a position in the esophagus proximate the ROI, the operator may adjust a rotational position of the first control wheel and/or the second control wheel to tilt the probe to the left or right and or the front or back of the patient, respectively, to orient a lens of the probe such that an ultrasound beam of the probe deflects off of a target object of the ROI at a perpendicular or close to perpendicular angle to acquire the medical image. The related information may be textual information that is displayed concurrently on the display device, which may include, as a non-limiting list of examples, a frequency of a signal generated by the ultrasound probe, a depth of the ultrasound probe with respect to the ROI, a time passed since a start of the examination, etc.

At 803, method 800 includes displaying a control wheel panel in the UI, such as the control wheel panel 414 of the graphical UI 400 of FIG. 4A. In one example, the control wheel panel may be a non-limiting example of the graphical control wheel display element 500 of FIG. 5A, which includes a first graphical control wheel display, which shows a rotational position of the first control wheel of the TEE control handle, and a second graphical control wheel display, which shows a rotational position of the second control wheel of the TEE control handle, as described above in reference to FIGS. 5A-5D. The first graphical control wheel display and the second graphical control wheel display may further indicate a state of a control wheel lock of the TEE control handle (e.g., the control wheel lock 206 of the handheld ultrasound device of FIG. 2A).

At 804, method 800 includes determining whether user input has been received via the first control wheel, the second control wheel, and/or the control wheel lock of the TEE control handle (e.g., by adjusting a rotational position the first control wheel, the second control wheel, or the control wheel lock). If at 804 it is determined that no user input has been received from the first control wheel, the second control wheel, and/or the control wheel lock, method 800 proceeds to 805. At 805, method 800 includes updating the ultrasound images generated by the probe and/or any related information in the UI until it is determined that user input has been received. If at 805 it is determined that user input has been received from the first control wheel, the second control wheel, and/or the control wheel lock, method 800 proceeds to 806.

At method 806, method 800 includes determining whether the rotational position of the first control wheel has been adjusted by the operator. For example, the operator may adjust the first control wheel by manipulating the first control wheel between a finger and thumb of the operator to rotate the first control wheel in a first direction (e.g., a clockwise direction), or to rotate the first control wheel in a second, opposite direction (e.g., a counterclockwise direction). If it is determined at 806 that the rotational position of the first control wheel has been adjusted, method 800 proceeds to 808. At 808, method 800 includes adjusting a first deflection indicator of the first graphical control wheel display in the UI. In one example, the first deflection indicator of the first graphical control wheel display is a non-limiting example of the deflection indicator 506 described in reference to FIGS. 5A, 5B, and 5C. In another example, the first deflection indicator of the first graphical control wheel display is a non-limiting example of the needle indicator 566 described in reference to FIG. 5D. In one example, adjusting the first deflection indicator includes adjusting a rotational position of the first deflection indicator around a circumference of the first graphical control wheel display in the first direction (e.g., clockwise) or in the second, opposite direction (e.g., counterclockwise), such that an indication point of the first deflection indicator extends outward from a center point of the first graphical control wheel display (e.g., as described above in relation to FIGS. 5A, 5B, 5C, and 5D).

If it is determined at 806 that the first control wheel has not been adjusted, or once the first deflection indicator of the first graphical control wheel display has been adjusted in the UI at 808, method 800 proceeds to 810. At 810, method 800 includes determining whether the rotational position of the second control wheel has been adjusted by the operator (e.g., in the first direction or the second, opposite direction). If it is determined at 810 that the rotational position of the second control wheel has been adjusted, method 800 proceeds to 812. At 812, method 800 includes adjusting a second deflection indicator of the second graphical control wheel display in the UI. In one example, the second deflection indicator of the second graphical control wheel display is a non-limiting example of the deflection indicator 514 described in reference to FIGS. 5A, 5B, and 5C. In another example, the second deflection indicator of the second graphical control wheel display is a non-limiting example of the needle indicator 576 described in reference to FIG. 5D. In one example, adjusting the second deflection indicator includes adjusting a rotational position of the second deflection indicator around a circumference of the second graphical control wheel display in the first direction or in the second, opposite direction, such that an indication point of the deflection indicator extends outward from a center point of the second graphical control wheel display (e.g., as described above in relation to FIGS. 5A, 5B, 5C, and 5D).

If it is determined at 810 that the second control wheel has not been adjusted, or once the second deflection indicator of the second graphical control wheel display has been adjusted in the UI at 812, method 800 proceeds to 814. At 814, method 800 includes determining whether the first control wheel has been locked via the control wheel lock. If it is determined at 814 that the first control wheel has been locked, method 800 proceeds to 816. At 816, method 800 includes adjusting a lock indicator (e.g., the lock indicator 508 of FIGS. 5A, 5B, 5C, and 5D) of the first graphical control wheel display in the UI. For example, adjusting the lock indicator of the first graphical control wheel display in the UI may include changing a graphical representation of a padlock to a graphical representation of an unlocked padlock, or changing a color of the graphical representation of the padlock, etc.

If it is determined at 814 that the first control wheel has not been locked, or once the lock indicator of the first graphical control wheel display has been adjusted in the UI at 816, method 800 proceeds to 818. At 818, method 800 includes determining whether the second control wheel has been locked via the control wheel lock. If it is determined at 818 that the second control wheel has been locked, method 800 proceeds to 820. At 820, method 800 includes adjusting a lock indicator (e.g., the lock indicator 518 of FIGS. 5A, 5B, and 5C) of the second graphical control wheel display in the UI.

At 822, method 800 includes adjusting and/or updating a first text label of the first graphical control wheel display, and adjusting and/or updating a second text label of the second graphical control wheel display in the UI. For example, as described above in reference to FIGS. 5A, 5B, and 5C, the first text label and/or the second text label may indicate that the first control wheel and/or the second control wheel, respectively, have been locked, or the first text label and/or the second text label may indicate a degree of deflection of the first control wheel and/or the second control wheel, respectively, or the first text label and/or the second text label may include a different indication to the operator (e.g., that a degree of deflection is high, etc.). It should be appreciated that the examples provided herein are for illustrative purposes, and other types of graphical or textual indicators may be included without departing from the scope of this disclosure. After adjusting and/or updating the text on the first control wheel display and the second control display, method 800 ends.

Thus, by allowing an operator of a medical imaging system to navigate a plurality of shortcut control elements visible in one or more display panels of a UI of a medical imaging system, via one or more controls arranged on a control handle of the medical imaging system (such as the TEE control handle described above), and select a shortcut control element associated with a desired functionality, an efficiency of the operator in performing an examination may be increased. Actions and functionalities available via a menu of the medical imaging system may be accessed in a more rapid and direct manner, and the operator may switch fluidly among modes of the medical imaging system, without having to look at the control handle or adjust a position and/or orientation of the control handle for purposes of viewing the one or more controls. By providing visual cues in the UI that indicate functionalities being executed or that may be executed during an examination, a cognitive load of the operator may be reduced (e.g., due to not having to remember a functional mapping of the one or more buttons of the control handle to one or more functionalities). Operator distraction may also be reduced, and a time taken for the examination may be reduced, thereby improving a patient experience and/or an outcome of the examination. Further, by facilitating a more efficient interaction with the UI, mechanical buttons of the control handle may be replaced with capacitive sensor buttons, reducing a cost of the medical imaging system and/or ultrasound probe. Additionally, by adjusting a display element of the UI to provide a visual indication of an angle of deflection of a probe of the medical imaging system in one or more planes of freedom, rather than relying on the operator to sense a configuration of a first control wheel and a second control wheel with a thumb and finger of the operator, the cognitive load of the operator may be further reduced and an efficiency of the operator may be increased.

The technical effect of allowing the operator to navigate among a plurality of display panels of the UI and access one or more shortcut control elements mapped to one or more functionalities of a medical imaging system is that operator efficiency may be increased, while a cognitive load and/or a distraction of the operator during the examination may be reduced.

The disclosure also provides support for a method for a medical imaging system, comprising: in response to an operator of the medical imaging system adjusting one or more controls arranged on a control handle of a handheld ultrasound device of the medical imaging system, adjusting a focus of a user interface (UI) of the medical imaging system among a plurality of graphical control elements displayed in the UI, and in response to the operator selecting a graphical control element of the plurality of graphical control elements at a location of the focus of the UI via the one or more controls, executing an action of the medical imaging system associated with the selected graphical control element. In a first example of the method, the one or more controls includes a selection button and at least one of a forward directional button, a back directional button, and a radial touchpad and a one-axis touchpad. In a second example of the method, optionally including the first example, at least one of the selection button, the forward directional button, and the back directional button is one of a capacitive sensor button, a resistive touch button, a shorting pad button, and a force-sensing resistor. In a third example of the method, optionally including one or both of the first and second examples, adjusting the one or more controls arranged on the control handle includes one of: the operator selecting the forward directional button or the back directional button, the operator dragging a thumb or a finger around the radial touchpad in a first rotational direction or a second, opposite rotational direction, and the operator dragging a thumb or a finger along the one-axis touchpad in a first direction or a second, opposite direction. In a fourth example of the method, optionally including one or more or each of the first through third examples, the plurality of graphical control elements is arranged in a plurality of display panels of the UI, and further comprising: in response to the operator adjusting the one or more controls arranged on the control handle in a first manner, adjusting the focus of the UI among the plurality of graphical control elements displayed in a selected display panel, in response to the operator selecting the selection button while adjusting the one or more controls in the first manner, selecting a graphical control element of the selected display panel, in response to the operator adjusting the one or more controls arranged on the control handle in a second manner, adjusting the focus of the UI among the plurality of display panels, and in response to the operator selecting the selection button while adjusting the one or more controls in the second manner, selecting a display panel. In a fifth example of the method, optionally including one or more or each of the first through fourth examples, adjusting the one or more controls arranged on the control handle in the first manner includes one of: the operator selecting a first directional button, the first directional button one of the back directional button and the forward directional button, and the operator dragging the thumb or the finger around the touchpad in a first direction, and wherein adjusting the one or more controls arranged on the control handle in the second manner includes one of: the operator selecting a second directional button, the second directional button indicating an opposite direction as the first directional button, and the operator dragging the thumb or the finger around the touchpad in a second, opposite direction. In a sixth example of the method, optionally including one or more or each of the first through fifth examples, the plurality of graphical control elements includes one or more shortcut control elements, and the action of the medical imaging system associated with each shortcut control element of the one or more shortcut control elements is a functionality available via a menu of the medical imaging system. In a seventh example of the method, optionally including one or more or each of the first through sixth examples, the functionality available via the menu of the medical imaging system initiates one of: a 2D mode of operation of the medical imaging system, a 3D mode of operation of the medical imaging system, a 4D mode of operation of the medical imaging system, a color mode of operation of the medical imaging system, and a Doppler mode of operation of the medical imaging system. In a eighth example of the method, optionally including one or more or each of the first through seventh examples, in response to the selection button being double-clicked by the operator, a predetermined shortcut control element of the one or more shortcut control elements is selected. In a ninth example of the method, optionally including one or more or each of the first through eighth examples, the predetermined shortcut control element saves a medical image displayed in the UI to an image store of the medical imaging system, and displays a thumbnail of the medical image in an image store panel of the UI. In a tenth example of the method, optionally including one or more or each of the first through ninth examples, the handheld ultrasound device is a trans-esophageal echocardiography (TEE) device, and the control handle is a TEE control handle.

The disclosure also provides support for a medical imaging system, comprising: an ultrasound probe coupled to a trans-esophageal echocardiography (TEE) control handle via an insertion tube with an articulated neck mechanism, a display device, a processor communicably coupled to the TEE control handle and the display device, and including instructions stored in a non-transitory memory that when executed cause the processor to: in response to an operator of the medical imaging system adjusting a first set of controls arranged on the TEE control handle: flex the articulated neck mechanism to adjust a position and/or orientation of the ultrasound probe, adjust a graphical display element of a user interface (UI) of the medical imaging system to indicate the adjusted position and/or orientation of the ultrasound probe, in response to the operator adjusting a second set of controls arranged on the TEE control handle in a first manner, adjust a focus of the UI between a plurality of display panels of the UI, in response to the operator adjusting the second set of controls in a second manner, adjust a focus of the UI between a plurality of control elements of the UI, indicate a location of the adjusted focus of the UI in the UI, in response to the operator selecting a control element at the location of the adjusted focus via the second set of controls, execute a functionality of the medical imaging system associated with the control element. In a first example of the system, the first set of controls includes a first control wheel and a second control wheel arranged on a first side of the TEE control handle, and wherein adjusting the graphical display element of the UI of the medical imaging system to indicate the adjusted position and/or orientation of the ultrasound probe includes: indicating a rotational position of the first control wheel on a graphical representation of the first control wheel, and indicating a rotational position of the second control wheel on a graphical representation of the second control wheel. In a second example of the system, optionally including the first example, further instructions are stored in the non-transitory memory that when executed cause the processor to indicate a state of a wheel lock of the first control wheel and the second control wheel, the state of the wheel lock one of: the first control wheel locked and the second control wheel unlocked, the first control wheel unlocked and the second control wheel locked, the first control wheel locked and the second control wheel locked, and the first control wheel unlocked and the second control wheel unlocked. In a third example of the system, optionally including one or both of the first and second examples, indicating the state of the wheel lock of the first control wheel and the second control wheel includes at least one of: displaying a graphical image of a padlock in a locked configuration on the graphical representation of the first control wheel responsive to the first control wheel being locked, displaying a graphical image of the padlock in an unlocked configuration on the graphical representation of the first control wheel responsive to the first control wheel being unlocked, displaying the graphical image of the padlock in a locked configuration on the graphical representation of the second control wheel responsive to the second control wheel being locked, displaying the graphical image of the padlock in an unlocked configuration on the graphical representation of the second control wheel responsive to the second control wheel being unlocked. In a fourth example of the system, optionally including one or more or each of the first through third examples, further instructions are stored in the non-transitory memory that when executed cause the processor to display text on one of the graphical representation of the first control wheel and the graphical representation of the second control wheel, where the text is one of an indication that the respective control wheel is locked and a degree of deflection of the ultrasound probe in a plane of freedom corresponding to the respective control wheel. In a fifth example of the system, optionally including one or more or each of the first through fourth examples, adjusting a graphical display element of the UI of the medical imaging system to indicate the adjusted position and/or orientation of the ultrasound probe include: adjusting a first rotational position indicator of a graphical representation of the first control wheel to indicate a degree of deflection of the probe in a first plane of freedom, and adjusting a second rotational position indicator on a graphical representation of the second control wheel to indicate a degree of deflection of the probe in a second plane of freedom. In a sixth example of the system, optionally including one or more or each of the first through fifth examples, the second set of controls includes a selection button and a radial touchpad on a second side of the TEE control handle, the second side different from the first side, and adjusting the second set of controls in the first manner includes scrolling with the radial touchpad in a first rotational direction, and adjusting the second set of controls in the second manner includes scrolling with the radial touchpad in a second rotational direction, the second rotational direction opposite the first rotational direction. In a seventh example of the system, optionally including one or more or each of the first through sixth examples, the second set of controls includes a capacitive sensor selection button, a capacitive sensor forward directional button, and a capacitive sensor back directional button arranged on a second side of the TEE control handle the second side different from the first side, and adjusting the second set of controls in the first manner includes selecting a first directional button, the first directional button one of the back directional button and the forward directional button, and adjusting the second set of controls in the second manner includes selecting a second directional button, the second directional button one of the back directional button and the forward directional button and different from the first directional button.

The disclosure also provides support for a method for a medical imaging system, comprising: in response to an operator of the medical imaging system selecting one or more shortcut control elements arranged on a control handle of a handheld ultrasound device of the medical imaging system, highlighting a selected shortcut control element of the one or more shortcut control elements in a graphical user interface (UI) of the medical imaging system, and in response to the operator selecting the selected shortcut control element a second time, executing a functionality of the medical imaging system associated with the selected shortcut control element.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for a medical imaging system, comprising:
   adjusting a position and/or an orientation of a probe of a handheld ultrasound device of the medical imaging system in response to an operator of the medical imaging system adjusting a first set of controls arranged on a control handle of the handheld ultrasound device, the first set of controls including a first control wheel configured to adjust deflection of a neck assembly including the probe in a first plane of freedom and a second control wheel configured to adjust deflection of the neck assembly in a second plane of freedom, and adjusting one or more graphical display elements of a user interface (UI) of the medical imaging system to indicate the adjusted position and/or orientation of the probe, the UI displayed on a display device of an ultrasound system coupled to the handheld ultrasound device via a cable, the one or more graphical display elements including a representation of the first control wheel and a representation of the second control wheel;
   in response to the operator of the medical imaging system adjusting a second set of controls arranged on the control handle, adjusting a focus of the UI displayed on the display device among a plurality of graphical control elements displayed in the UI; and
   in response to the operator selecting a graphical control element of the plurality of graphical control elements at a location of the focus of the UI via the second set of controls, executing an action of the medical imaging system associated with the selected graphical control element.

2. The method of claim 1, wherein the second set of controls includes a selection button and at least one of a forward directional button, a back directional button, and a radial touchpad and a one-axis touchpad, wherein the representation of the first control wheel includes a first circle with a first angle indicator and the representation of the second control wheel includes a second circle with a second angle indicator.

3. The method of claim 2, wherein at least one of the selection button, the forward directional button, and the back directional button is one of a capacitive sensor button, a resistive touch button, a shorting pad button, and a force-sensing resistor, and wherein adjusting the one or more graphical display elements of the UI to indicate the adjusted position and/or orientation of the probe comprises adjusting the first angle indicator to indicate a current deflection angle of the neck assembly in the first plane of freedom and/or adjusting the second angle indicator to indicate a current deflection angle of the neck assembly in the second plane of freedom.

4. The method of claim 2, wherein adjusting the second set controls arranged on the control handle includes one of:
the operator selecting the forward directional button or the back directional button;
the operator entering an input around the radial touchpad in a first rotational direction or a second, opposite rotational direction; and
the operator entering an input along the one-axis touchpad in a first direction or a second, opposite direction,
wherein the representation of the first control wheel further includes a first lock indicator configured to indicate a lock state of the first control wheel, and the representation of the second control wheel further includes a second lock indicator configured to indicate a lock state of the second control wheel.

5. The method of claim 2, wherein the plurality of graphical control elements is arranged in a plurality of display panels of the UI, and further comprising:
in response to the operator adjusting the second set of controls arranged on the control handle in a first manner, adjusting the focus of the UI displayed on the display device among the plurality of graphical control elements displayed in a selected display panel;
in response to the operator selecting the selection button while adjusting the second set of controls in the first manner, selecting a graphical control element of the selected display panel;
in response to the operator adjusting the second set of controls arranged on the control handle in a second manner, adjusting the focus of the UI displayed on the display device among the plurality of display panels; and
in response to the operator selecting the selection button while adjusting the second set of controls in the second manner, selecting a display panel.

6. The method of claim 5, wherein:
adjusting the second set of controls arranged on the control handle in the first manner includes one of:
the operator selecting a first directional button, the first directional button comprising one of the back directional button and the forward directional button; and
the operator entering the input around the touchpad in a first direction; and
adjusting the second set of controls arranged on the control handle in the second manner includes one of:
the operator selecting a second directional button, the second directional button indicating an opposite direction as the first directional button; and
the operator entering the input around the radial touchpad in a second, opposite direction.

7. The method of claim 2, wherein the plurality of graphical control elements includes one or more shortcut control elements, and the action of the medical imaging system associated with each shortcut control element of the one or more shortcut control elements is a functionality available via a menu of the medical imaging system.

8. The method of claim 7, wherein the functionality available via the menu of the medical imaging system initiates one of:
a 2D mode of operation of the medical imaging system;
a 3D mode of operation of the medical imaging system;
a 4D mode of operation of the medical imaging system;
a color mode of operation of the medical imaging system; and
a Doppler mode of operation of the medical imaging system.

9. The method of claim 7, wherein in response to the selection button being double-clicked by the operator, a predetermined shortcut control element of the one or more shortcut control elements is selected.

10. The method of claim 9, wherein the predetermined shortcut control element, when selected, causes a medical image displayed in the UI to be saved to an image store of the medical imaging system, and a thumbnail of the medical image to be displayed in an image store panel of the UI, and wherein the handheld ultrasound device is a trans-esophageal echocardiography (TEE) device and the control handle is a TEE control handle.

11. A medical imaging system, comprising:
an ultrasound probe coupled to a trans-esophageal echocardiography (TEE) control handle via an insertion tube with an articulated neck mechanism, the articulated neck mechanism configured to flex to adjust a position and/or orientation of the ultrasound probe in response to an operator of the medical imaging system adjusting a first set of controls arranged on the TEE control handle; and
an ultrasound device coupled to the TEE control handle via a cable, the ultrasound device comprising a display device and a processor communicably coupled to the TEE control handle and the display device, and including instructions stored in a non-transitory memory that when executed cause the processor to:
in response to the operator adjusting the first set of controls, adjust a graphical display element of a user interface (UI) displayed on the display device to indicate the adjusted position and/or orientation of the ultrasound probe;
in response to the operator adjusting a second set of controls arranged on the TEE control handle in a first manner, adjust a focus of the UI displayed on the display device between a plurality of display panels of the UI;
in response to the operator adjusting the second set of controls in a second manner, adjust a focus of the UI displayed on the display device between a plurality of control elements included within a selected display panel of the plurality of display panels of the UI;
indicate a location of the adjusted focus of the UI in the UI displayed on the display device; and
in response to the operator selecting a control element of the plurality of control elements at the location of the adjusted focus via the second set of controls, execute a functionality of the medical imaging system associated with the control element.

12. The system of claim 11, wherein the first set of controls includes a first control wheel and a second control wheel arranged on a first side of the TEE control handle, and wherein adjusting the graphical display element of the UI to indicate the adjusted position and/or orientation of the ultrasound probe includes:
indicating a rotational position of the first control wheel on a graphical representation of the first control wheel displayed on the display device; and
indicating a rotational position of the second control wheel on a graphical representation of the second control wheel displayed on the display device.

13. The system of claim 12, wherein further instructions are stored in the non-transitory memory that when executed cause the processor to indicate a state of a wheel lock of the first control wheel and the second control wheel, the state of the wheel lock one of:

the first control wheel locked and the second control wheel unlocked;

the first control wheel unlocked and the second control wheel locked;

the first control wheel locked and the second control wheel locked; and the first control wheel unlocked and the second control wheel unlocked.

14. The system of claim 13, wherein indicating the state of the wheel lock of the first control wheel and the second control wheel includes at least one of:

displaying, on the display device, a graphical image of a padlock in a locked configuration on the graphical representation of the first control wheel responsive to the first control wheel being locked;

displaying, on the display device, a graphical image of the padlock in an unlocked configuration on the graphical representation of the first control wheel responsive to the first control wheel being unlocked;

displaying, on the display device, the graphical image of the padlock in a locked configuration on the graphical representation of the second control wheel responsive to the second control wheel being locked; and displaying, on the display device, the graphical image of the padlock in an unlocked configuration on the graphical representation of the second control wheel responsive to the second control wheel being unlocked.

15. The system of claim 12, wherein further instructions are stored in the non-transitory memory that when executed cause the processor to display, on the display device, text on one of the graphical representation of the first control wheel and the graphical representation of the second control wheel, where the text is one of an indication that the respective control wheel is locked and a degree of deflection of the ultrasound probe in a plane of freedom corresponding to the respective control wheel.

16. The system of claim 12, wherein adjusting a graphical display element of the UI to indicate the adjusted position and/or orientation of the ultrasound probe includes:

adjusting a first rotational position indicator of a graphical representation of the first control wheel displayed on the display device to indicate a degree of deflection of the probe in a first plane of freedom; and adjusting a second rotational position indicator on a graphical representation of the second control wheel displayed on the display device to indicate a degree of deflection of the probe in a second plane of freedom.

17. The system of claim 12, wherein the second set of controls includes a selection button and a radial touchpad on a second side of the TEE control handle, the second side different from the first side, and adjusting the second set of controls in the first manner includes scrolling with the radial touchpad in a first rotational direction, and adjusting the second set of controls in the second manner includes scrolling with the radial touchpad in a second rotational direction, the second rotational direction opposite the first rotational direction, and wherein the plurality of display panels comprises a shortcut panel, a virtual track ball interface, and an image store panel.

18. The system of claim 12, wherein the second set of controls includes a capacitive sensor selection button, a capacitive sensor forward directional button, and a capacitive sensor back directional button arranged on a second side of the TEE control handle, the second side different from the first side, and adjusting the second set of controls in the first manner includes selecting a first directional button, the first directional button one of the back directional button and the forward directional button, and adjusting the second set of controls in the second manner includes selecting a second directional button, the second directional button one of the back directional button and the forward directional button and different from the first directional button.

19. The system of claim 11, wherein the instructions are further executable to, in response to the operator selecting a representation of the functionality listed in a menu displayed on the display device using a separate input device, execute the functionality of the medical imaging system.

20. A method for a medical imaging system, comprising:

in response to an operator of the medical imaging system selecting one or more controls arranged on a control handle of a handheld ultrasound device of the medical imaging system, highlighting a selected shortcut control element of one or more shortcut control elements in a graphical user interface (UI) of the medical imaging system, and in response to the operator selecting the selected shortcut control element via the one or more controls, executing a functionality of the medical imaging system associated with the selected shortcut control element, wherein each of the one or more shortcut control elements duplicates an existing functionality of the ultrasound imaging system available via a menu of the ultrasound imaging system.

\* \* \* \* \*